US011541490B2

(12) United States Patent
Nageswaran et al.

(10) Patent No.: US 11,541,490 B2
(45) Date of Patent: Jan. 3, 2023

(54) ANEURYSM TREATMENT DEVICE

(71) Applicant: Covidien LP, Mansfield, MA (US)

(72) Inventors: Ashok Nageswaran, Irvine, CA (US); Junwei Li, Irvine, CA (US); Hoai Nguyen, Westminster, CA (US); Andyanhdzung Huynh, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/949,565

(22) Filed: Nov. 3, 2020

(65) Prior Publication Data

US 2021/0128161 A1    May 6, 2021

Related U.S. Application Data

(60) Provisional application No. 62/930,333, filed on Nov. 4, 2019, provisional application No. 62/930,421, filed
(Continued)

(51) Int. Cl.
*A61B 17/12* (2006.01)
*A61B 17/00* (2006.01)
(Continued)

(52) U.S. Cl.
CPC ........ *B23P 19/047* (2013.01); *A61B 17/1214* (2013.01); *A61B 17/12031* (2013.01);
(Continued)

(58) Field of Classification Search
CPC ........ A61B 17/12031; A61B 17/12145; A61B 17/1214; A61B 17/12172;
(Continued)

(56) References Cited

U.S. PATENT DOCUMENTS 5,261,916 A * 11/1993 Engelson ......... A61B 17/12022
606/1
5,601,600 A * 2/1997 Ton .................. A61B 17/12022
606/198

(Continued)

FOREIGN PATENT DOCUMENTS

CA        3031482 A1    8/2017
CN      105105812 A   12/2015
(Continued)

OTHER PUBLICATIONS

International Search Report and Written Opinion dated Feb. 17, 2021, International Application No. PCT/US20/70741, 6 pages.
(Continued)

*Primary Examiner* — Shaun L David
(74) *Attorney, Agent, or Firm* — Fortem IP LLP

(57) ABSTRACT

Treatment of aneurysms can be improved by use of a treatment system including a conduit have a distal portion, a coupler slidably coupled to the distal portion, an occlusive member coupled to the coupler, and a securing member coupled to the conduit proximal to the coupler. The securing member can include a distal end portion that is removably coupled to the coupler. In some embodiments, the securing member can have a shape and/or be treated such that the securing member self-expands to decouple itself from the coupler during deployment of the occlusive member. In some embodiments, movement of the conduit relative to the coupler causes the securing member to decouple from the coupler.

19 Claims, 18 Drawing Sheets

Related U.S. Application Data on Nov. 4, 2019, provisional application No. 62/930,487, filed on Nov. 4, 2019, provisional application No. 62/930,357, filed on Nov. 4, 2019, provisional application No. 62/930,303, filed on Nov. 4, 2019, provisional application No. 62/930,324, filed on Nov. 4, 2019.

(51) Int. Cl.
*A61B 90/00* (2016.01)
*B23P 19/04* (2006.01)

(52) U.S. Cl.
CPC .. *A61B 17/12113* (2013.01); *A61B 17/12145* (2013.01); *A61B 17/12172* (2013.01); *A61B 17/12186* (2013.01); *A61B 17/12168* (2013.01); *A61B 2017/00526* (2013.01); *A61B 2017/00557* (2013.01); *A61B 2017/00862* (2013.01); *A61B 2017/00929* (2013.01); *A61B 2017/12054* (2013.01); *A61B 2017/12063* (2013.01); *A61B 2090/376* (2016.02); *A61B 2090/3966* (2016.02)

(58) Field of Classification Search
CPC ........ A61B 17/12113; A61B 17/12186; A61B 17/12168; A61B 17/12181; A61B 17/12022; A61B 17/12027; A61B 17/12036; A61B 17/1204; A61B 17/12099; A61B 17/12122; A61B 17/12131; A61B 17/12177; A61B 17/0057; A61B 2017/00557; A61B 2017/00862; A61B 2017/12054; A61B 2017/00929; A61B 2017/12063; A61B 2017/00526; A61B 2017/1209; A61B 2017/00575; A61B 2017/00632; A61B 2017/00646; A61B 2017/00654; A61B 2017/1205; A61B 2017/12095; B23P 19/047
USPC ....................................... 606/200
See application file for complete search history.

(56) References Cited

U.S. PATENT DOCUMENTS

| | | | |
|---|---|---|---|
| 5,916,235 A | | 6/1999 | Guglielmi |
| 6,936,058 B2 | | 8/2005 | Forde et al. |
| 7,473,266 B2 | | 1/2009 | Glaser |
| 7,879,065 B2 | | 2/2011 | Gesswein et al. |
| 8,372,062 B2 | | 2/2013 | Murphy et al. |
| 8,690,936 B2 | | 4/2014 | Nguyen et al. |
| 9,339,275 B2 | | 5/2016 | Trommeter et al. |
| 9,713,475 B2 | | 7/2017 | Divino et al. |
| 9,918,718 B2 | | 3/2018 | Lorenzo |
| 10,130,372 B2 | | 11/2018 | Griffin |
| 10,932,933 B2 | | 3/2021 | Bardsley et al. |
| 10,952,740 B2* | | 3/2021 | Dasnurkar ....... A61B 17/12172 |
| 11,076,860 B2* | | 8/2021 | Lorenzo ........... A61B 17/12145 |
| 11,134,953 B2* | | 10/2021 | Solaun ................. A61B 17/12 |
| 11,179,159 B2 | | 11/2021 | Cox et al. |
| 2001/0000797 A1* | | 5/2001 | Mazzocchi ....... A61B 17/0057 606/151 |
| 2004/0176798 A1 | | 9/2004 | Foy et al. |
| 2004/0236344 A1 | | 11/2004 | Monstadt et al. |
| 2005/0038470 A1 | | 2/2005 | Van et al. |
| 2005/0119684 A1* | | 6/2005 | Guterman ....... A61B 17/12186 606/198 |
| 2006/0064151 A1 | | 3/2006 | Guterman et al. |
| 2006/0276824 A1* | | 12/2006 | Mitelberg ....... A61B 17/12154 606/200 |
| 2006/0276829 A1* | | 12/2006 | Balgobin ........ A61B 17/12154 606/200 |
| 2007/0179520 A1* | 8/2007 | West ............... A61B 17/1214 606/200 |
| 2007/0186933 A1* | 8/2007 | Domingo ........ A61B 17/12104 606/205 |
| 2007/0198075 A1* | 8/2007 | Levy ..................... A61F 2/82 623/1.11 |
| 2007/0221230 A1* | 9/2007 | Thompson ...... A61B 17/12031 128/207.15 |
| 2007/0299461 A1* | 12/2007 | Elliott ............. A61B 17/1215 606/191 |
| 2008/0119886 A1* | 5/2008 | Greenhalgh ..... A61B 17/12172 606/200 |
| 2008/0221554 A1* | 9/2008 | O'Connor ....... A61B 17/12145 604/526 |
| 2008/0221703 A1* | 9/2008 | Que ................ A61B 17/12022 623/23.65 |
| 2008/0281350 A1 | 11/2008 | Sepetka et al. |
| 2008/0283066 A1* | 11/2008 | Delgado ................ A61B 5/076 606/1 |
| 2009/0036877 A1* | 2/2009 | Nardone ......... A61B 17/12022 606/1 |
| 2009/0099592 A1* | 4/2009 | Buiser .............. A61B 17/1214 606/53 |
| 2009/0287294 A1* | 11/2009 | Rosqueta ........ A61B 17/12113 623/1.15 |
| 2010/0023048 A1 | 1/2010 | Mach |
| 2010/0121350 A1* | 5/2010 | Mirigian ........ A61B 17/12113 606/142 |
| 2011/0144669 A1 | 6/2011 | Becking et al. |
| 2011/0238041 A1 | 9/2011 | Lim et al. |
| 2012/0123510 A1* | 5/2012 | Liungman .............. A61F 2/954 623/1.11 |
| 2012/0143301 A1* | 6/2012 | Maslanka ....... A61B 17/12109 623/1.11 |
| 2013/0066357 A1 | 3/2013 | Aboytes et al. |
| 2013/0073026 A1 | 3/2013 | Russo et al. |
| 2013/0138136 A1* | 5/2013 | Beckham ........ A61B 17/12136 29/520 |
| 2013/0211495 A1* | 8/2013 | Halden ........... A61B 17/12109 623/1.12 |
| 2014/0039542 A1* | 2/2014 | Trommeter ..... A61B 17/12109 606/200 |
| 2014/0135811 A1 | 5/2014 | Divino et al. |
| 2014/0200607 A1 | 7/2014 | Sepetka et al. |
| 2014/0215792 A1 | 8/2014 | Leopold et al. |
| 2014/0257360 A1 | 9/2014 | Keillor |
| 2015/0005808 A1 | 1/2015 | Chouinard et al. |
| 2015/0272589 A1* | 10/2015 | Lorenzo ......... A61B 17/12145 606/200 |
| 2015/0313605 A1 | 11/2015 | Griffin |
| 2015/0335333 A1 | 11/2015 | Jones et al. |
| 2015/0343181 A1* | 12/2015 | Bradway ........ A61B 17/12031 604/103.1 |
| 2016/0022445 A1 | 1/2016 | Ruvalcaba et al. |
| 2016/0106437 A1* | 4/2016 | van der Burg ... A61B 17/12122 606/200 |
| 2016/0128699 A1* | 5/2016 | Hadley ................ A61F 2/0108 606/200 |
| 2016/0331381 A1 | 11/2016 | Ma |
| 2017/0105739 A1 | 4/2017 | Dias et al. |
| 2017/0156734 A1 | 6/2017 | Griffin |
| 2017/0224350 A1* | 8/2017 | Shimizu ........... A61B 17/1214 |
| 2017/0354421 A1* | 12/2017 | Maguire ......... A61B 17/12109 |
| 2017/0367713 A1 | 12/2017 | Greene et al. |
| 2018/0070955 A1* | 3/2018 | Greene, Jr. ..... A61B 17/12109 |
| 2018/0110797 A1 | 4/2018 | Li et al. |
| 2018/0132856 A1* | 5/2018 | Wierzbicki ............. A61L 31/14 |
| 2018/0140305 A1 | 5/2018 | Connor |
| 2018/0206852 A1 | 7/2018 | Moeller |
| 2018/0242979 A1 | 8/2018 | Lorenzo |
| 2018/0256171 A1* | 9/2018 | Chow .............. A61B 17/12159 |
| 2018/0317932 A1* | 11/2018 | H'Doubler ...... A61M 25/10182 |
| 2019/0008522 A1* | 1/2019 | Lorenzo ........ A61B 17/12172 |
| 2019/0009057 A1* | 1/2019 | Li ........................ A61B 1/05 |
| 2019/0053807 A1* | 2/2019 | Tassoni ........... A61B 17/12022 |
| 2019/0223876 A1 | 7/2019 | Badruddin et al. |
| 2019/0223881 A1* | 7/2019 | Hewitt .............. A61B 17/1215 |

(56) References Cited

U.S. PATENT DOCUMENTS

| | | |
|---|---|---|
| 2019/0343532 A1 | 11/2019 | Divino et al. |
| 2019/0351107 A1* | 11/2019 | Sawhney ......... A61B 17/12186 |
| 2020/0138448 A1* | 5/2020 | Dasnurkar ....... A61B 17/00491 |
| 2020/0268392 A1* | 8/2020 | Choi ................ A61B 17/12109 |
| 2021/0128160 A1 | 5/2021 | Li et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0153872 A1 | 5/2021 | Nguyen et al. |
| 2021/0161643 A1* | 6/2021 | Totten .............. A61B 17/12172 |
| 2021/0196284 A1 | 7/2021 | Gorochow et al. |
| 2021/0212698 A1 | 7/2021 | Connor |

FOREIGN PATENT DOCUMENTS

| | | | |
|---|---|---|---|
| EP | 2468348 B1 | 10/2016 | |
| WO | 9905977 A1 | 2/1999 | |
| WO | 03011151 A1 | 2/2003 | |
| WO | 2007079402 A2 | 7/2007 | |
| WO | 2015166013 A1 | 11/2015 | |
| WO | WO-2018022186 A1 * | 2/2018 | ....... A61B 17/12113 |
| WO | 2018050262 A1 | 3/2018 | |
| WO | 2019038293 A1 | 2/2019 | |

OTHER PUBLICATIONS

International Search Report and Written Opinion dated Feb. 23, 2021, International Application No. PCT/US20/70743, 14 pages.

International Search Report and Written Opinion dated Apr. 13, 2021, International Application No. PCT/US20/70742, 18 pages.

* cited by examiner

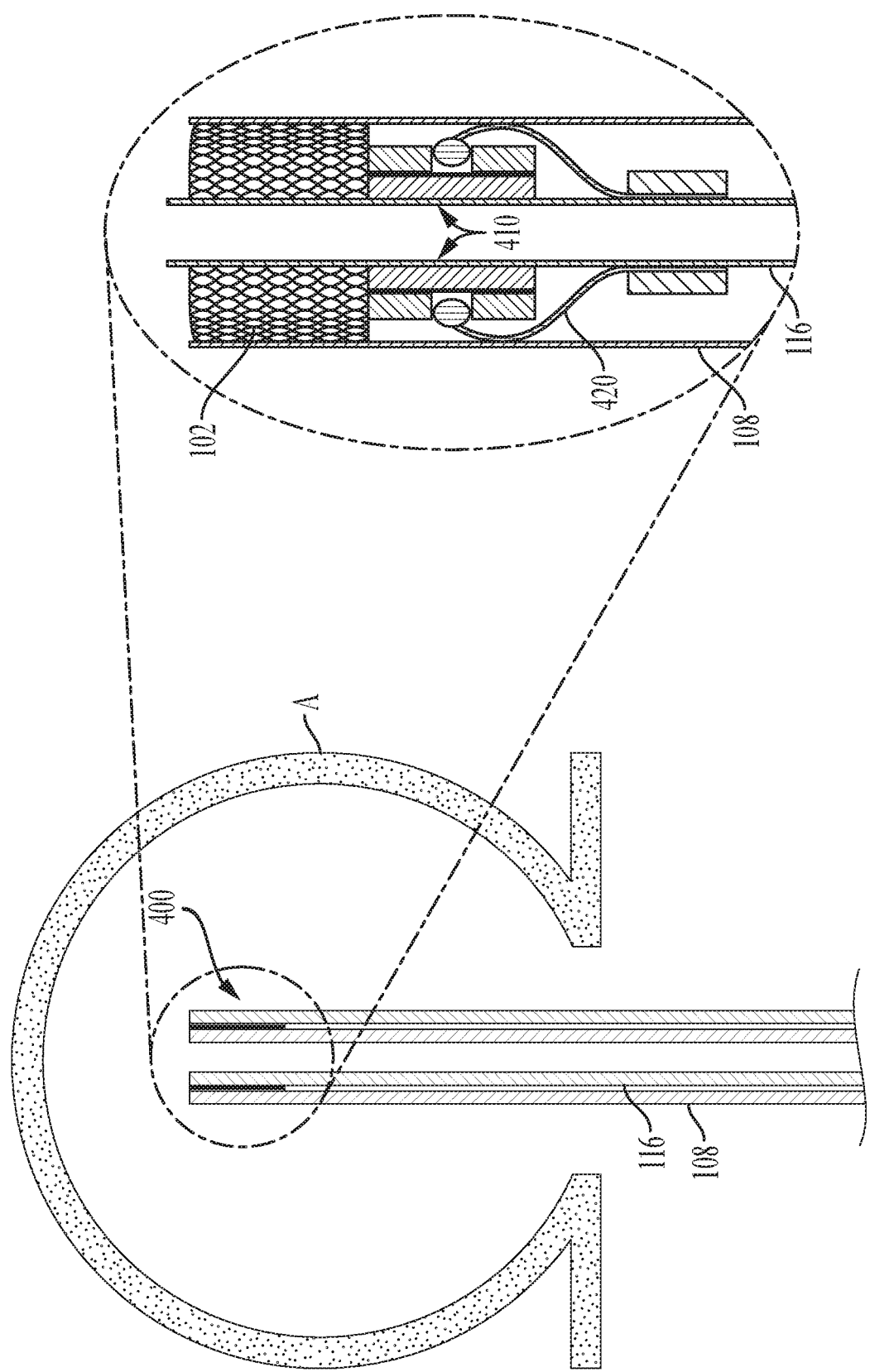

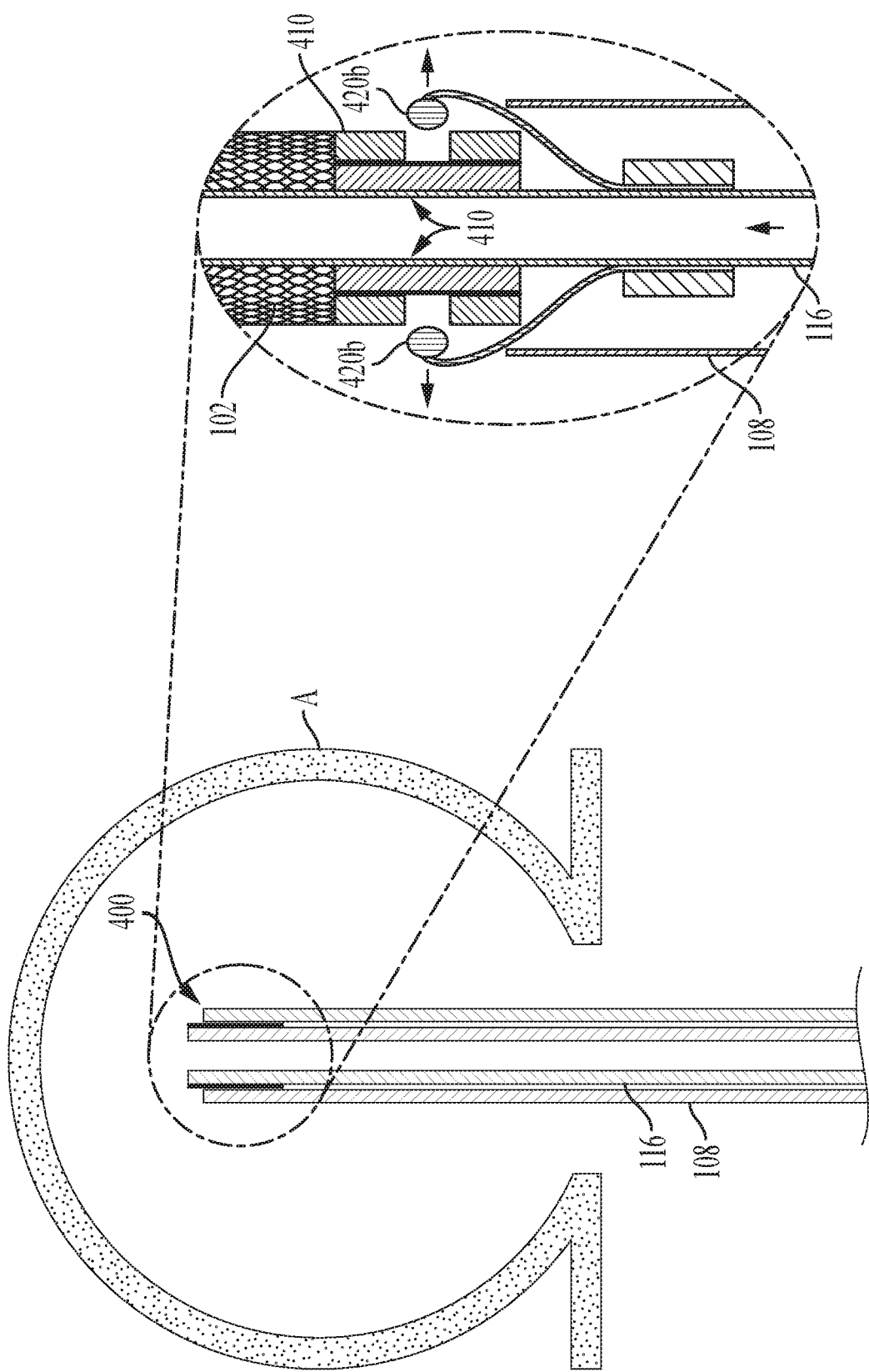

ANEURYSM TREATMENT DEVICE

CROSS-REFERENCE TO RELATED APPLICATIONS

The present application claims the benefit of priority of U.S. Provisional Application No. 62/930,421, filed Nov. 4, 2019, U.S. Provisional Application No. 62/930,487, filed Nov. 4, 2019, U.S. Provisional Application No. 62/930,303, filed Nov. 4, 2019, U.S. Provisional Application No. 62/930,324, filed Nov. 4, 2019, U.S. Provisional Application No. 62/930,333, filed Nov. 4, 2019, and U.S. Provisional Application No. 62/930,357, filed Nov. 4, 2019, each of which is incorporated by reference herein in its entirety.

The following applications are also incorporated by reference herein in their entireties: U.S. patent application Ser. No. 16/949,567, filed Nov. 3, 2020, and titled DEVICES, SYSTEMS, AND METHODS FOR TREATMENT OF INTRACRANIAL ANEURYSMS; U.S. patent application Ser. No. 16/949,568, filed Nov. 3, 2020, and titled DEVICES, SYSTEMS, AND METHODS FOR TREATMENT OF INTRACRANAL ANEURYSMS; U.S. patent application Ser. No. 16/949,561, filed Nov. 3, 2020, and titled SYSTEMS AND METHODS FOR TREATING ANEURYSMS; U.S. patent application Ser. No. 16/949,563, filed Nov. 3, 2020, and titled SYSTEMS AND METHODS FOR TREATING ANEURYSMS; U.S. patent application Ser. No. 16/949,564, filed Nov. 3, 2020, and titled SYSTEMS AND METHODS FOR TREATING ANEURYSMS; U.S. patent application Ser. No. 16/949,569, filed Nov. 3, 2020, and titled DEVICES, SYSTEMS, AND METHODS FOR TREATMENT OF INTRACRANIAL ANEURYSMS; U.S. patent application Ser. No. 16/949,566, filed Nov. 3, 2020, and titled SYSTEMS AND METHODS FOR TREATING ANEURYSMS; U.S. patent application Ser. No. 16/949,570, filed Nov. 3, 2020, and titled DEVICES, SYSTEMS, AND METHODS FOR TREATING ANEURYSMS; International Application No. PCT/US2020/070743, filed Nov. 3, 2020, titled DEVICES, SYSTEMS, AND METHODS FOR TREATMENT OF INTRACRANIAL ANEURYSMS; International Application No. PCT/US2020/070741, filed Nov. 3, 2020, titled DEVICES, SYSTEMS, AND METHODS FOR TREATMENT OF INTRACRANIAL ANEURYSMS; and International Application No. PCT/US2020/070742, filed Nov. 3, 2020, titled SYSTEMS AND METHODS FOR TREATING ANEURYSMS.

TECHNICAL FIELD

The present technology relates to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The subject technology is illustrated, for example, according to various aspects described below, including with reference to FIGS. 1A-8H. Various examples of aspects of the subject technology are described as numbered clauses (1, 2, 3, etc.) for convenience. These are provided as examples and do not limit the subject technology.

Clause 1. A treatment device, comprising:
a conduit having a distal portion and a lumen extending therethrough;
a coupler slidably coupled to the distal portion such that the coupler is axially movable relative to the conduit;
an occlusive member coupled to the coupler; and
a securing member coupled to the conduit proximal to the coupler, the securing member including a distal end portion removably coupled to the coupler.

Clause 2. The treatment device of Clause 1, wherein movement of the conduit relative to the coupler causes the securing member to decouple from the coupler.

Clause 3. The treatment device of any one of the previous Clauses, wherein distal movement of the conduit relative to the coupler causes the distal end portion of the securing member to move radially away from the coupler.

Clause 4. The treatment device of any one of the preceding Clauses, wherein the securing member includes a proximal end portion coupled to the conduit, and wherein movement of the conduit in a distal direction relative to the coupler causes the distal end portion of the securing member to move radially away from the coupler.

Clause 5. The treatment device of any one of the preceding Clauses, wherein the securing member comprises at least one of an elastic material, Nitinol, stainless steel, cobalt chromium, platinum, or alloys thereof.

Clause 6. The treatment device of any one of the preceding Clauses, wherein the distal end portion of the securing member has a radial dimension larger than that of the rest of the securing member.

Clause 7. The treatment device of any one of the preceding Clauses, wherein the distal end portion comprises an atraumatic end.

Clause 8. The treatment device of any one of the preceding Clauses, wherein the securing member comprises a continuous surface extending along its entire length.

Clause 9. The treatment device of any one of the preceding Clauses, wherein the securing member is heat treated to have a concave and/or convex shape.

Clause 10. The treatment device of any one of the preceding Clauses, wherein the securing member is heat treated such that at least a portion of the securing member is curved inwardly toward the conduit and/or coupler.

Clause 11. The treatment device of any one of the preceding Clauses, wherein at least a portion of the securing member proximal to the distal end portion is substantially linear or straight.

Clause 12. The treatment device of any one of the preceding Clauses, wherein the securing member is a first securing member, the treatment device further comprising a second securing member coupled to the conduit proximal to the coupler, the second securing member including a distal end portion configured to be removably coupled to the coupler.

Clause 13. The treatment device of any one of the preceding Clauses, wherein the securing member surrounds a circumference of the conduit.

Clause 14. The treatment device of any one of the preceding Clauses, wherein the securing member includes a proximal end portion coupled to the conduit.

Clause 15. The treatment device of any one of the preceding Clauses, wherein the securing member includes a proximal end portion coupled to the conduit, the treatment device further comprising a stop fixedly coupled to the conduit proximal the coupler, wherein the proximal end portion of the securing member is coupled to the conduit via the stop.

Clause 16. The treatment device of any one of the preceding Clauses, wherein the coupler is rotatably moveable relative to the conduit.

Clause 17. The treatment device of any of the previous Clauses, wherein the coupler is disposed around an outermost surface of the conduit.

Clause 18. The treatment device of any one of the preceding Clauses, wherein the coupler has a substantially curved, circular, polygonal or hexagonal shape.

Clause 19. The treatment device of any one of the preceding Clauses, wherein a proximal end portion of the occlusive member is coupled to the distal portion of the conduit via the coupler.

Clause 20. The treatment device of any one of the preceding Clauses, wherein at least a portion of the coupler is a radiopaque marker.

Clause 21. The treatment device of any one of the preceding Clauses, wherein the coupler includes an intermediate region that is recessed relative to a proximal region of the coupler.

Clause 22. The treatment device of any Clause 21, wherein a dimension of the intermediate region is approximately the same or larger than a dimension of the distal end portion of the securing member.

Clause 23. The treatment device of Clause 21 or Clause 22, wherein the distal end portion of the securing member is positioned at least partially within the intermediate region such that the securing member is removably coupled to the coupler via the distal end portion.

Clause 24. The treatment device of any one of the preceding Clauses, wherein the coupler comprises an inner band and an outer band at least partially surrounding the inner band, wherein a portion of the occlusive member is coupled to the coupler between the inner and outer bands.

Clause 25. The treatment device of any one of Clause 24, wherein the outer band includes a first outer band and a second outer band spaced apart from the first outer band to define an intermediate region therebetween.

Clause 26. The treatment device of Clause 25, wherein a dimension of the intermediate region is approximately the same or larger than a dimension of the distal end portion of the securing member.

Clause 27. The treatment device of Clause 25 or Clause 26, wherein the distal end portion of the securing member is positioned at least partially within the intermediate region such that the securing member is removably coupled to the coupler via the distal end portion.

Clause 28. The treatment device of any one of the preceding Clauses, wherein the conduit is a hypotube or tubular element.

Clause 29. The treatment device of Clause 28, wherein the hypotube or tubular element extends at least partially through the occlusive member and/or distally beyond the occlusive member.

Clause 30. The treatment device of Clause 28 or Clause 29, wherein the hypotube or tubular element has a cross-sectional dimension of at least 0.012 inches.

Clause 31. The treatment device of any one of Clause 28-Clause 30, wherein the tubular element is a microcatheter.

Clause 32. The treatment device of Clause 31, wherein the microcatheter has a cross-sectional dimension of at least 0.035 inches.

Clause 33. The treatment device of Clause 1-Clause 27, wherein the conduit is a microcatheter or tubular element.

Clause 34. The treatment device of Clause 33, wherein the microcatheter has a cross-sectional dimension of at least 0.012 inches.

Clause 35. The treatment device of any one of the preceding Clauses, wherein the occlusive member is an occlusive member or intrasaccular device configured to be implanted within an aneurysm.

Clause 36. The treatment device of any one of the preceding Clauses, wherein the occlusive member is disposed around the conduit and coupled to an outer surface of the conduit via the coupler.

Clause 37. The treatment device of any one of the preceding Clauses, wherein the occlusive member comprises an expandable mesh having a constrained state for delivery to an aneurysm and an expanded state in which at least a portion of the mesh is configured to be disposed across a neck of the aneurysm.

Clause 38. The treatment device of Clause 37, wherein the expandable mesh comprises a plurality of braided filaments that assume a pre-set, three-dimensional shape in the expanded state.

Clause 39. The treatment device of any one of Clause 37 or Clause 38, wherein the expandable mesh comprises a braid formed of 24, 32, 36, 48, 64, or 72 filaments.

Clause 40. The treatment device of any one of Clause 37-Clause 39, wherein the expandable mesh comprises a braid formed of a plurality of wires, some or all of which have a diameter of at least 0.001 inches.

Clause 41. The treatment device of any one of Clause 37-Clause 40, wherein the expandable mesh comprises a braid formed of a plurality of wires, some or all of which have the same diameter.

Clause 42. The treatment device of any one of Clause 37-Clause 40, wherein the expandable mesh comprises a braid formed of a plurality of wires, at least some of which have different diameters.

Clause 43. The treatment device of any one of the Clause 37-Clause 42, wherein, in the expanded state, the expandable mesh forms one of a sphere, a prolate spheroid, or an oblate spheroid.

Clause 44. The treatment device of any one of Clause 37-Clause 43, wherein the expandable mesh comprises an inner layer and an outer layer.

Clause 45. The treatment device of any one of Clause 37-Clause 44, wherein the expandable mesh has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

Clause 46. The treatment device of any one of Clause 37-Clause 45, wherein the expandable mesh is a laser-cut tube.

Clause 47. The treatment device of any one of Clause 37-Clause 46, wherein the expandable mesh comprises a plurality of interwoven filaments.

Clause 48. The treatment device of any one of the previous Clauses, wherein the occlusive member is curved along at least a majority of its entire length.

Clause 49. The treatment device of any one of the previous Clauses, wherein the occlusive member is collapsible when contacted by a synthetic gel or fluid.

Clause 50. The treatment device of any one of the preceding Clauses, wherein the occlusive member is configured to rotate about the conduit.

Clause 51. The treatment device of any one of the preceding Clauses, wherein the occlusive member is rotatably and slidably coupled to the conduit.

Clause 52. The treatment device of any one of the preceding Clauses, wherein the occlusive member has an aperture at a distal portion thereof, and wherein the elongated member extends through the aperture.

Clause 53. The treatment device of any one of the preceding Clauses, wherein the occlusive member is configured to move axially along the elongated member.

Clause 54. The treatment device of any one of the preceding Clauses, further comprising an embolic element, wherein the conduit is configured to convey the embolic element to a target site.

Clause 55. The treatment device of Clause 54, wherein the embolic element is a liquid embolic.

Clause 56. The treatment device of Clause 54 or Clause 55, wherein the embolic element comprises a biopolymer and/or a chemical crosslinking agent.

Clause 57. The treatment device of any one of Clause 54-Clause 56, wherein the biopolymer includes chitosan, a derivative of chitosan, an analog of chitosan, or a combination thereof.

Clause 58. The treatment device of Clause 54-Clause 57, wherein the chemical crosslinking agent includes genipin, a derivative of genipin, an analog of genipin, or a combination thereof.

Clause 59. A treatment system comprising:
the treatment device of any one of Clause 1-Clause 58; and
an elongated shaft having a lumen extending therethrough, wherein the treatment device is configured to be slidably disposed within the lumen of the elongated shaft.

Clause 60. A treatment system comprising:
the treatment device of any one of Clause 1-Clause 58;
a first elongated shaft having a first lumen extending therethrough, wherein the treatment device is configured to be slidably disposed within the first lumen; and
a second elongated shaft having a second lumen extending therethrough, wherein the first elongated shaft is configured to be slidably disposed within the second lumen.

Clause 61. The treatment system of Clause 60, wherein the first elongated shaft is a microcatheter and the second elongated shaft is a delivery or guide catheter.

Clause 62. A method for treating an aneurysm, comprising:
providing the treatment device of any one of the preceding clauses.

Clause 63. The method of Clause 62, further comprising:
positioning a distal end of the conduit of the treatment device in an aneurysm cavity; and
releasing the occlusive member of the treatment device from the conduit while the distal end of the conduit is positioned within the aneurysm cavity such that the occlusive member self-expands to assume an expanded state.

Clause 64. The method of Clause 63, wherein releasing the occlusive member comprises decoupling the securing member of the treatment device from the coupler of the treatment device.

Clause 65. The method of Clause 64, wherein the securing member includes a distal end portion coupled to the coupler while the distal end of the conduit is positioned within the aneurysm cavity, and wherein decoupling the securing member comprises decoupling the distal end portion of the securing member by distally moving the conduit relative to the coupler.

Clause 66. The method of any one of the preceding Clauses, wherein positioning the distal end of the conduit comprises advancing the distal end of the conduit toward a dome or distalmost end of the aneurysm, such that the distal end of the conduit extends beyond a distal terminus of a microcatheter surrounding the conduit.

Clause 67. The method of Clause 66, wherein the distal end of the conduit, after positioning, is in a first position, the method further comprising, after positioning the distal end of the conduit, repositioning the conduit by (i) retracting the distal end of the conduit away from the dome or distalmost end of the aneurysm, and (ii) after retracting, advancing the distal end of conduit toward the dome or distalmost end of the aneurysm such that the distal end has a second position different than the first position.

Clause 68. The method of Clause 67, wherein retracting the distal end comprises retracting the distal end to be proximal to the distal terminus of the catheter.

Clause 69. The method of Clause 67 or Clause 68, wherein advancing the distal end to the second position comprises advancing the distal end without withdrawing the guide or delivery catheter from the patient.

Clause 70. The method of any one of the preceding Clauses, wherein in the first expanded state the occlusive member forms a predetermined three-dimensional shape.

Clause 71. The method of any one of the preceding Clauses, wherein in the first expanded state the occlusive member defines a first hollow interior.

Clause 72. The method of Clause 71, further comprising delivering an embolic element between the occlusive member and a wall of the aneurysm to transform the occlusive member into a second expanded state in which the occlusive member defines a second hollow interior having a second volume less than the first volume.

Clause 73. The method of Clause 72, wherein in the second expanded state the occlusive member forms a three-dimensional shape different than the three-dimensional shape in the first expanded state.

Clause 74. The method of Clause 72 or Clause 73, wherein transforming the occlusive member into the second expanded state includes injecting the embolic element to urge a portion of a sidewall of the occlusive member in a direction away from a wall of the aneurysm and toward the first hollow interior.

Clause 75. The method of any one of Clause 72-Clause 74, wherein transforming the occlusive member into the second expanded state includes injecting the embolic element to invert a portion of a sidewall of the occlusive member such that the portion is convex towards the aneurysm wall in the first expanded state and concave towards the aneurysm wall in the second expanded state.

Clause 76. The method of any one of Clause 72-Clause 75, wherein delivering the embolic element occurs after the occlusive member is in the first expanded state.

Clause 77. The method of any one of Clause 72-Clause 76, wherein the occlusive member has a globular or generally spherical shape in the first expanded state.

Clause 78. The method of any one of Clause 72-Clause 77, wherein the occlusive member is cup or bowl-shaped in the second expanded state.

Clause 79. The method of any one of Clause 72-Clause 78, wherein the second expanded state is a predetermined three-dimensional shape.

Clause 80. The method of any one of Clause 72-Clause 79, wherein the occlusive member forms a multi-layer braid at the neck of the aneurysm in the second expanded state.

Clause 81. The method of any one of the preceding Clauses, wherein the occlusive member is an occlusive material, an expandable mesh, and/or a braid.

Clause 82. The method of any one of the preceding Clauses, wherein the occlusive member is a dual-layered braid.

Clause 83. The method of any one of the previous Clauses, wherein the occlusive member is a mesh.

Clause 84. The method of any one of the previous Clauses, wherein the occlusive member is a braid.

Clause 85. The method of any one of the previous Clauses, wherein the occlusive member is a dual-layered braid.

Clause 86. The method of any one of the previous Clauses, wherein the occlusive member has a globular or generally spherical shape in the first expanded state.

Clause 87. The method of any one of the previous Clauses, wherein the occlusive member is cup or bowl-shaped in the second expanded state.

Clause 88. The method of any one of the previous Clauses, wherein the second shape is a predetermined three-dimensional shape.

Clause 89. The method of any one of the previous Clauses, wherein the occlusive member forms a multi-layer braid at the neck of the aneurysm in the second expanded state.

Clause 90. The method of any one of the previous Clauses, wherein the occlusive member comprises a plurality of braided filaments that assume a pre-set, three-dimensional shape in the expanded state.

Clause 91. The method of any one of the previous Clauses, wherein the occlusive member comprises a braid formed of 24, 32, 36, 48, 64, or 72 filaments.

Clause 92. The method of any one of the previous Clauses, wherein the occlusive member comprises a braid formed of a plurality of wires, some or all of which have a diameter of about 0.001 inches (0.00254 cm).

Clause 93. The method of any one of the previous Clauses, wherein the occlusive member comprises a braid formed of a plurality of wires, some or all of which have the same diameter.

Clause 94. The method of any one of the previous Clauses, wherein the occlusive member comprises a braid formed of a plurality of wires, at least some of which have different diameters.

Clause 95. The method of any one of the previous Clauses, wherein the occlusive member forms a closed, globular shape in the expanded state, the mesh having an aperture at a distal portion.

Clause 96. The method of any one of the previous Clauses, wherein, in the expanded state, the occlusive member forms one of a sphere, a prolate spheroid, or an oblate spheroid.

Clause 97. The method of any one of the previous Clauses, wherein the occlusive member comprises an inner layer and an outer layer.

Clause 98. The method of any one of the previous Clauses, wherein the occlusive member comprises an inner layer and an outer layer that meet at a fold at a distal portion of the occlusive member.

Clause 99. The method of any one of the previous Clauses, wherein the expandable mesh includes an aperture at a distal portion, the aperture being defined by the fold.

Clause 100. The method of any one of the previous Clauses, wherein the occlusive member comprises an inner layer and an outer layer that meet at a fold at a proximal portion of the occlusive member.

Clause 101. The method of any one of the previous Clauses, wherein the expandable mesh includes an aperture at a distal portion, the aperture being defined by the fold.

Clause 102. The method of any one of the previous Clauses, wherein the occlusive member has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

Clause 103. The method of any one of the previous Clauses, wherein the occlusive member is formed of a plurality of filaments having first and second ends fixed at a coupler.

Clause 104. The method of any one of the previous Clauses, wherein the occlusive member is formed of a plurality of filaments formed of an inner core material surrounded by an outer material.

Clause 105. The method of any one of the previous Clauses, wherein the inner core material is a radiopaque material and the outer material is a superelastic material.

Clause 106. The method of any one of the previous Clauses, wherein the occlusive member is a laser-cut tube.

Clause 107. The method of any one of the previous Clauses, wherein the occlusive member comprises a plurality of filaments.

Clause 108. The method of any one of the previous Clauses, wherein the filaments are interwoven.

Clause 109. The method of any one of the previous Clauses, wherein the filaments are braided.

Clause 110. The method of any one of the previous Clauses, wherein each of the filaments has a first end and a second end opposite the first end, and wherein both the first and second ends of the filaments are fixed relative to one another at a coupler.

Clause 111. The method of Clause 110, wherein the coupler is disposed at a distal end of the occlusive member.

Clause 112. The method of Clause 110 or Clause 111, wherein the coupler is disposed at a proximal end of the occlusive member.

Clause 113. The method of any one of the previous Clauses, wherein each of the filaments terminate at only one end of the distal element.

Clause 114. The method of any one of the previous Clauses, wherein the filaments form an opening at an end of the distal element opposite the only one end.

Clause 115. The method of any one of the previous Clauses, wherein an inverted portion of each of the filaments define the opening.

Clause 116. The method of any one of the previous Clauses, wherein the inverted portions of the filaments are configured to move relative to one another.

Clause 117. The method of any one of the previous Clauses, wherein the embolic element comprises a biopolymer and a chemical crosslinking agent.

Clause 118. The method of any one of the previous Clauses, wherein the biopolymer includes chitosan, a derivative of chitosan, an analog of chitosan, or a combination thereof.

Clause 119. The method of any one of the previous Clauses, wherein the chemical crosslinking agent includes genipin, a derivative of genipin, an analog of genipin, or a combination thereof.

Clause 120. The method of any one of the previous Clauses, wherein the embolic element further comprises a physical crosslinking agent.

Clause 121. The method of any one of the previous Clauses, the physical crosslinking agent includes β glycerophosphate, a derivative of β glycerophosphate, an analog of β glycerophosphate, or a combination thereof.

Clause 122. The method of any one of the previous Clauses, wherein
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β glycerophosphate, a derivative of β glycerophosphate, an analog of β glycerophosphate, or a combination thereof.

Clause 123. The method of any one of the previous Clauses, wherein the embolic element comprises a contrast agent.

Clause 124. The method of any one of the previous Clauses, wherein the contrast agent is selected to provide diminishing radiopacity.

Clause 125. The method of any one of the previous Clauses, wherein the contrast agent includes iohexol, a derivative of iohexol, an analog of iohexol, or a combination thereof.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIGS. 8A-8H are cross-sectional side views of a method for delivering, repositioning, and/or resheathing a treatment device via the assembly shown in FIG. 4A, in accordance with embodiments of the present technology.

DETAILED DESCRIPTION

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Specific details of systems, devices, and methods for treating intracranial aneurysms in accordance with embodiments of the present technology are described herein with reference to FIGS. 1A-8H. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. Overview of Systems of the Present Technology

Figure 1A:
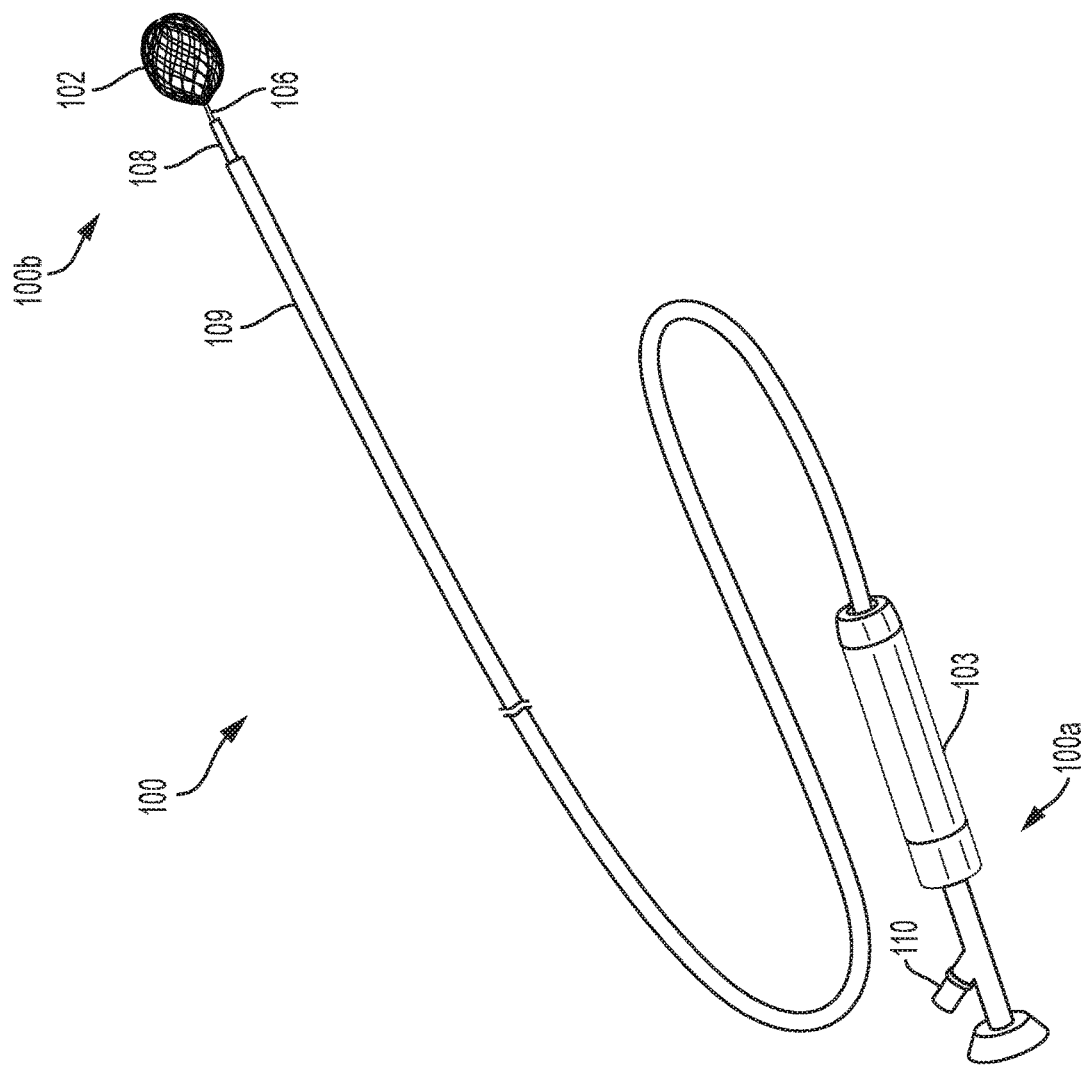
FIG. 1A shows a perspective view of a system for treating an aneurysm in accordance with the present technology.

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100a configured to be extracorporeally positioned during treatment and a distal portion 100b configured to be intravascularly positioned within a blood vessel (such as an intracranial blood vessel) at a treatment site at or proximate an aneurysm. The treatment system 100 may include a handle 103 at the proximal portion 100a, the occlusive member 102 at the distal portion 100b, and a plurality of elongated shafts or members extending between the proximal and distal portions 100a and 100b. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

Figure 1B:
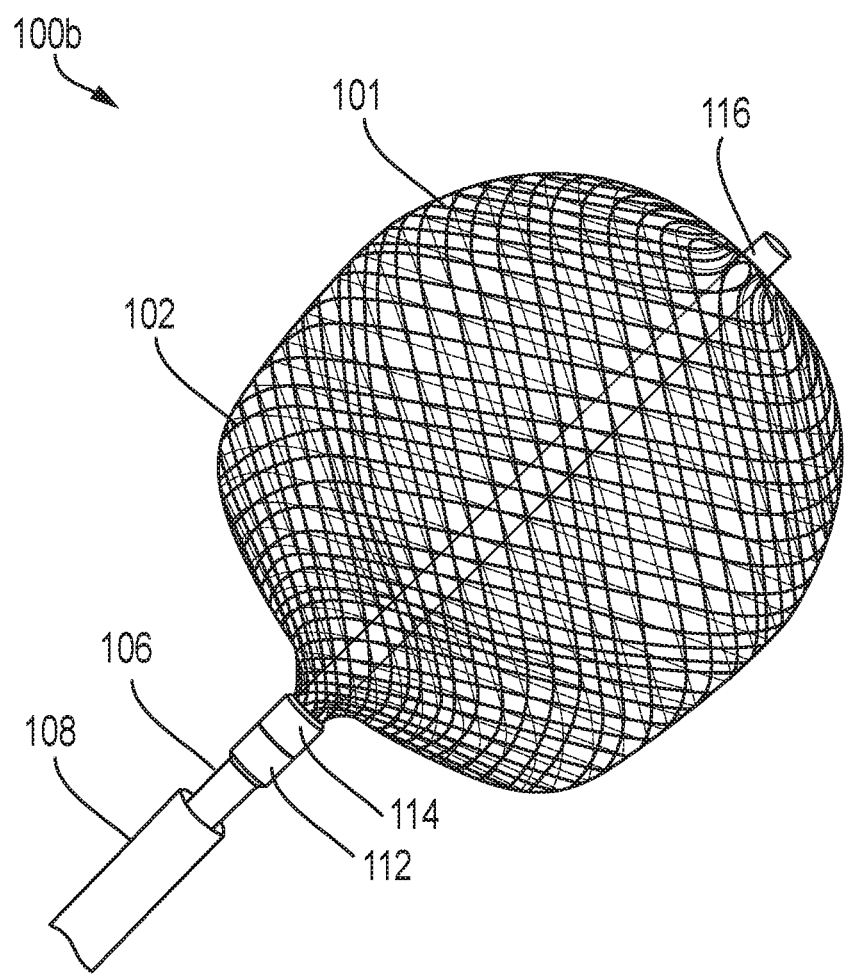
FIG. 1B shows an enlarged view of a distal portion of the treatment system of FIG. 1A in accordance with the present technology.

FIG. 1B is an enlarged view of the distal portion 100b of the treatment system 100. Referring to FIGS. 1A and 1B together, the occlusive member 102 may be detachably coupled to a distal end of the elongated member 106. For example, the elongated member 106 may include a first coupler 112 at its distal end, and the occlusive member 102 may include a second coupler 114 configured to detachably couple with the first coupler 112. The treatment system 100 may further comprise a conduit 116 extending from the handle 103 (for example, via port 110) distally to the distal portion 100b of the treatment system 100. The conduit 116 is configured to deliver the embolic element (and/or one or more precursors thereof) through one or more components of the delivery system (e.g., the first or second elongated shafts 109, 108, the elongated member 106, etc.) to a position at the exterior of the occlusive member 102. As such, the embolic element may be positioned between the occlusive member 102 and an inner wall of the aneurysm cavity, as described in greater detail below.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongated shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise a solid metal wire. In some embodiments, the elongated member 106 may comprise any other suitable form of shaft such as an elongated tubular shaft.

In some embodiments, the elongated member 106 can comprise stainless steel, nitinol, or other metal or alloy. In some embodiments, the elongated member 106 can be surrounded over some or all of its length by a coating, such as, for example, polytetrafluoroethylene. The elongated member 106 may have a diameter that is generally constant along its length, or the elongated member 106 may have a diameter that tapers radially inwardly, along at least a portion of its length, as it extends in a distal direction.

According to several embodiments, the conduit 116 may be a catheter or elongated shaft that is delivered separately from the second elongated shaft 108.

A. Selected Examples of Occlusive Members

Figure 1C:
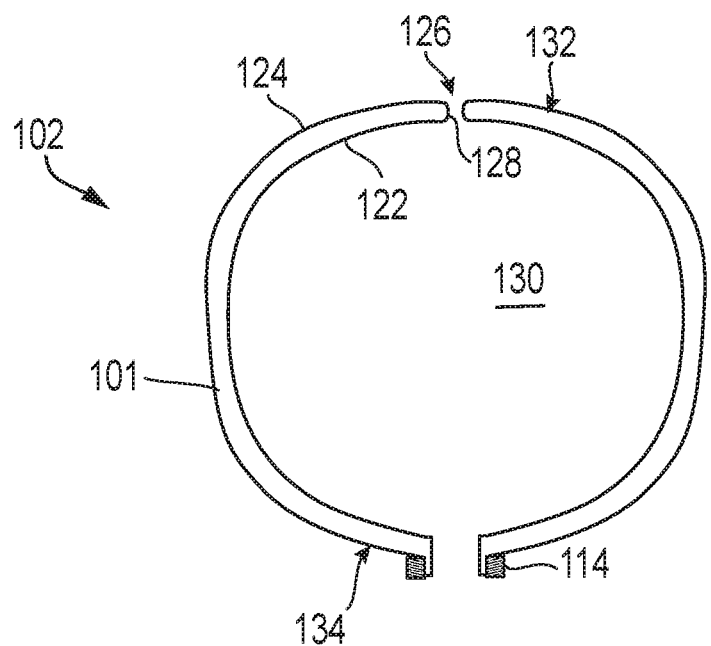
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
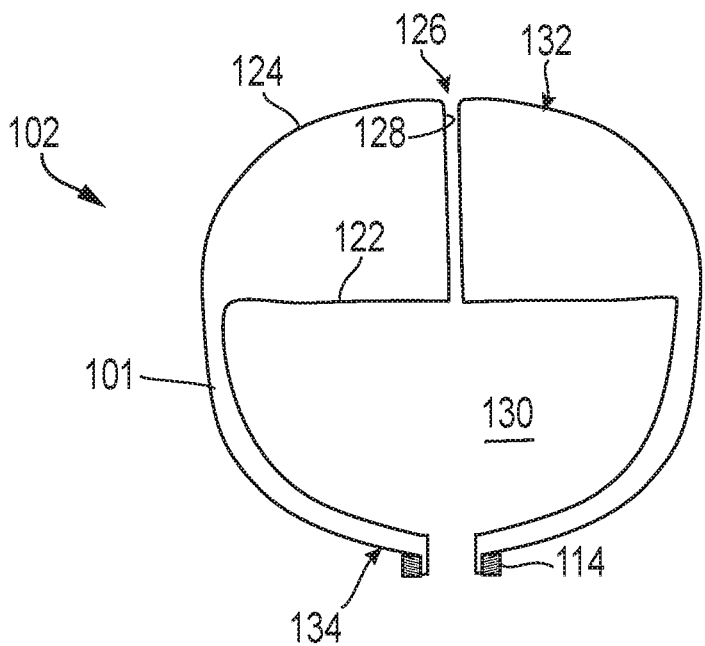
Figure 2:
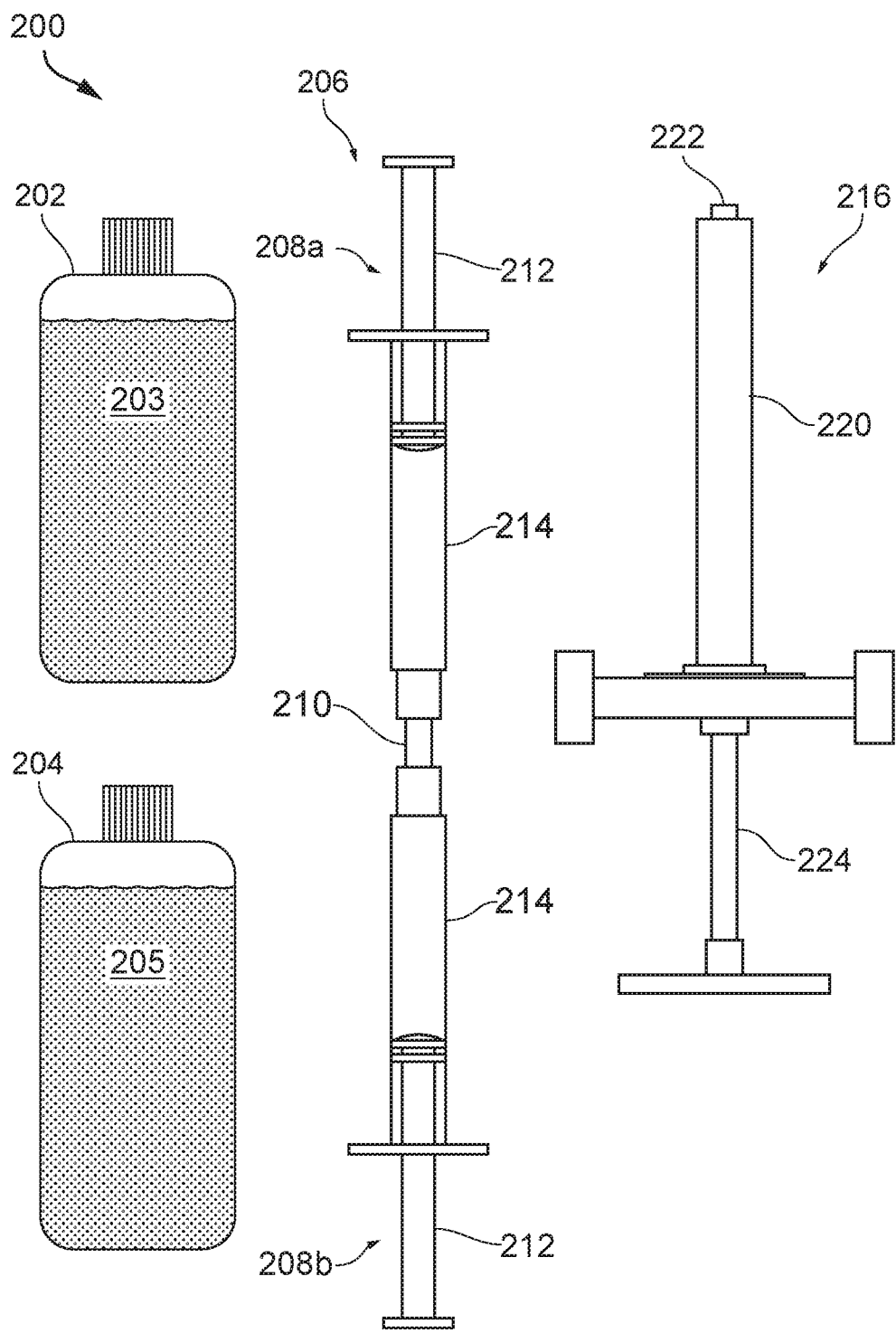
FIG. 2 shows an embolic kit according to the present technology.

In any case, the inner layer 124 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusion member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to the at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208*a*, 208*b*)

and a coupler 210 extending between respective exit ports (not shown) of the mixing syringes 208. The mixing syringes 208a, 208b each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100b of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the system 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include β glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

II. Selected Methods for Treating Aneurysms

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state.

Figure 3A:
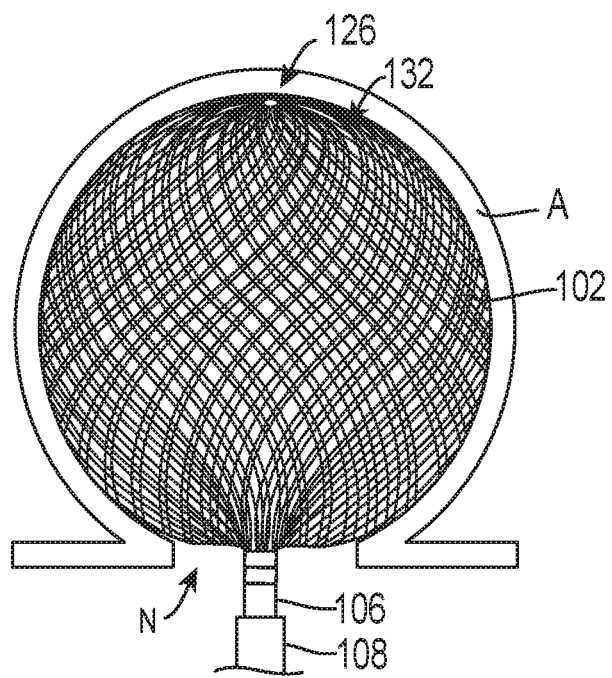
FIGS. 3A-3G depict an example method of treating an aneurysm with the treatment system of the present technology.
Figure 3B:
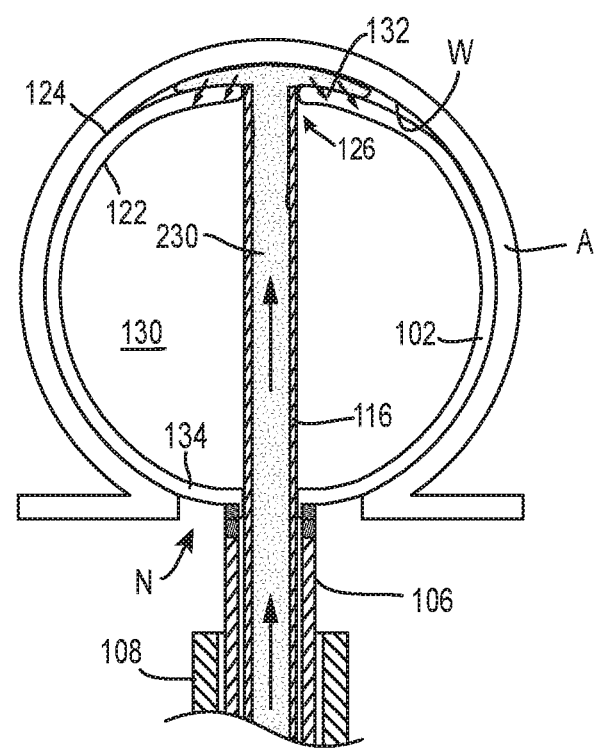

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
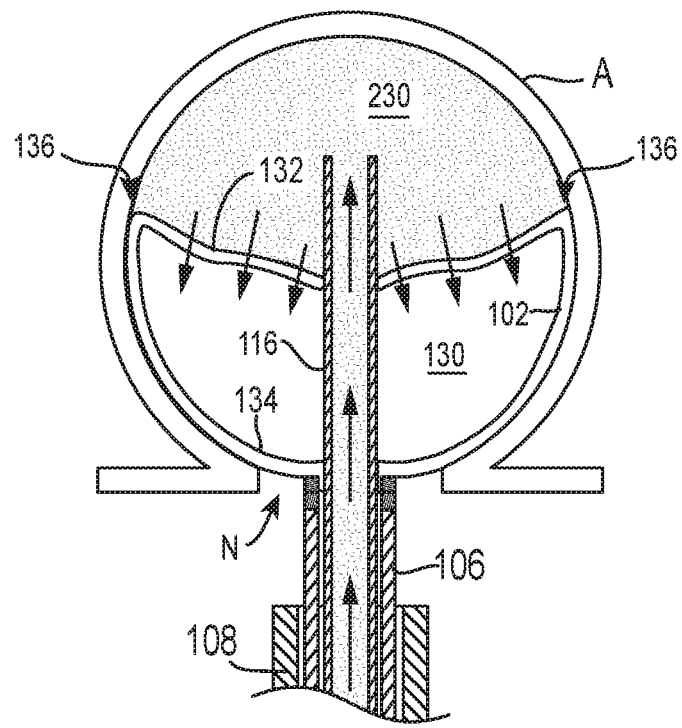
Figure 3D:
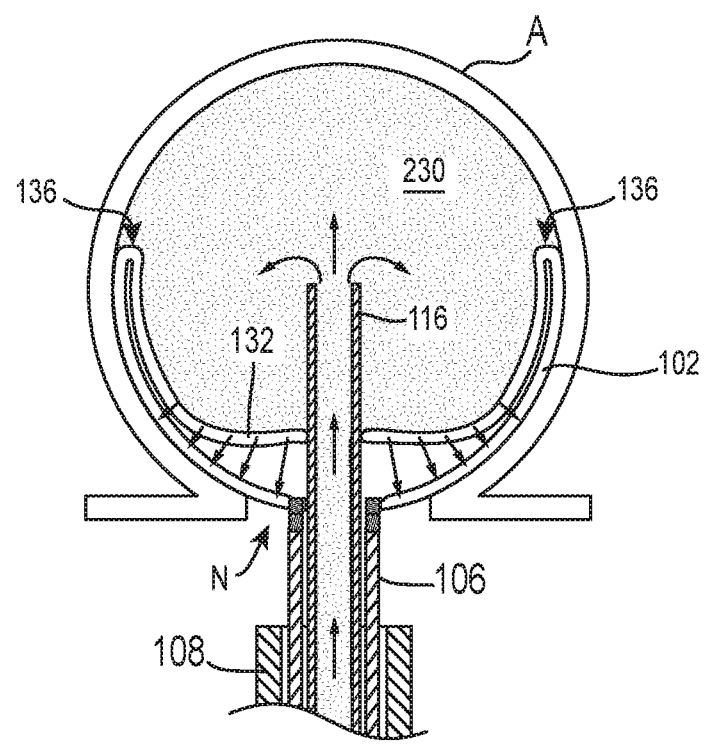

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. Additional details regarding devices, systems, and methods for monitoring and/or confirming deployment are described below with reference to FIGS. 4A-5B. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figure 3E:
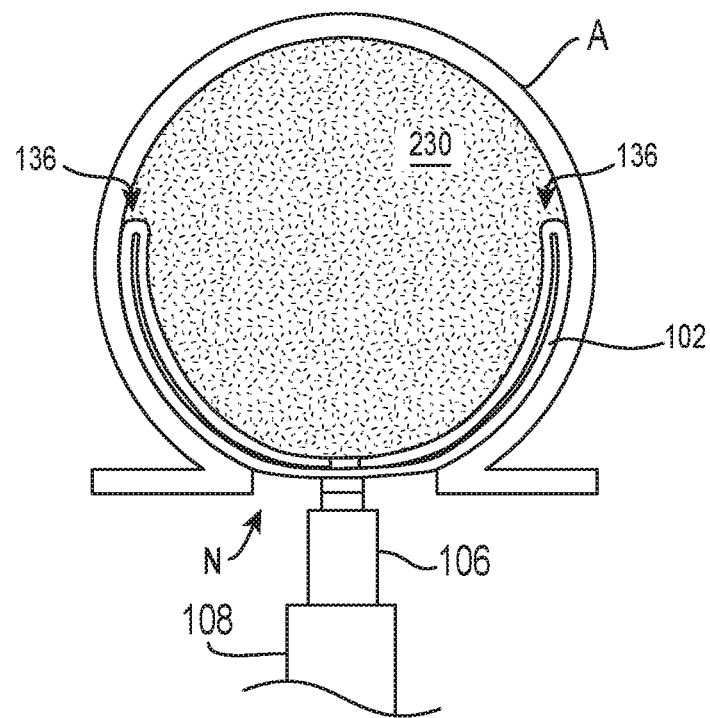
Figure 3F:
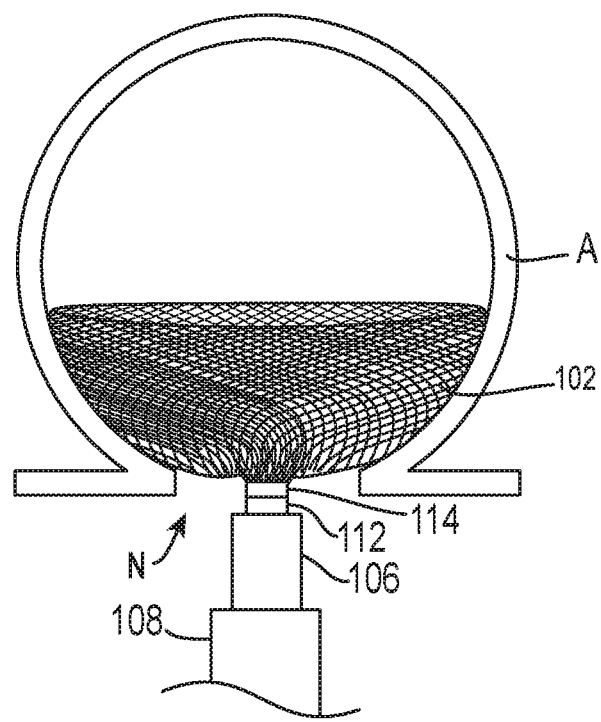

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusion member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
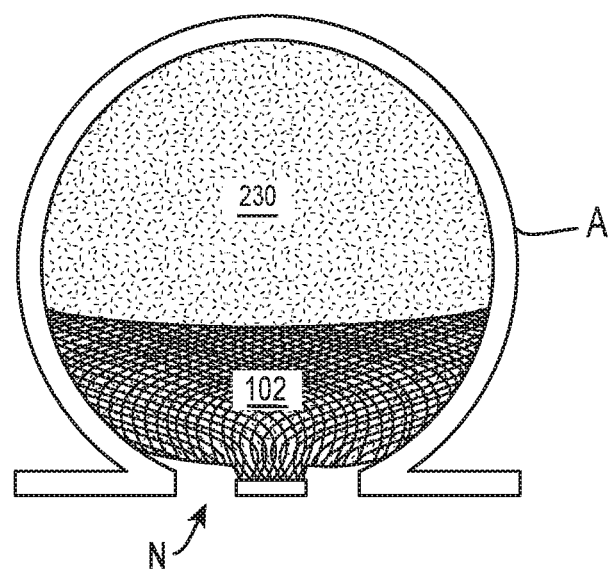

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive device 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. Example Treatment Devices and Methods of Use

Figure 4A:
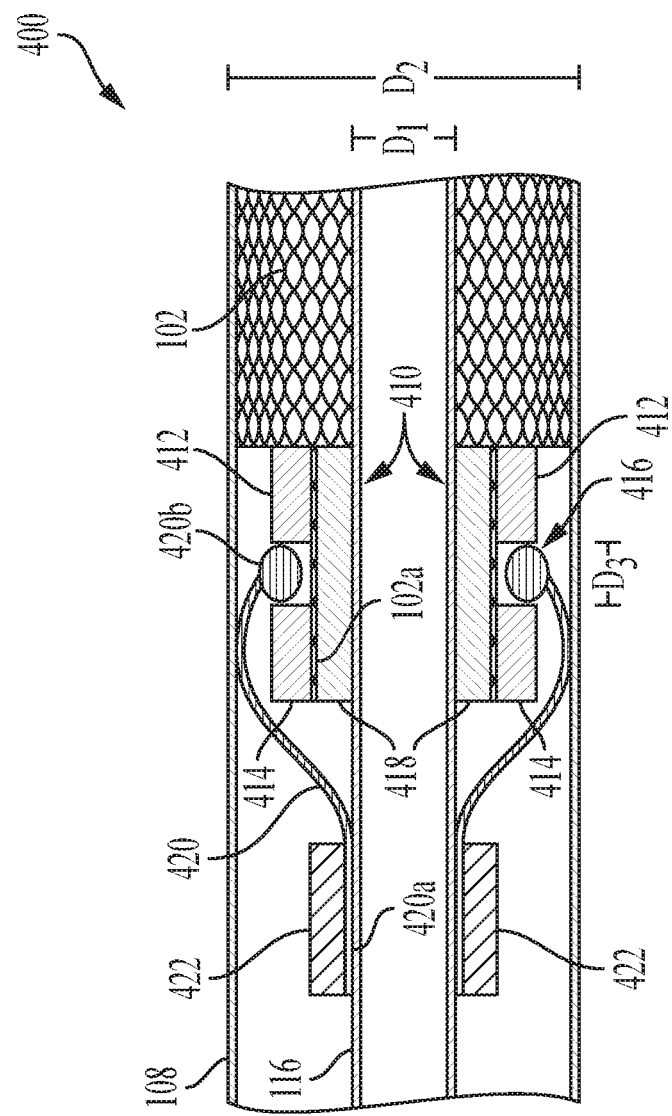
FIG. 4A is a cross-sectional side view of a coupling assembly, in accordance with embodiments of the present technology.
Figure 4B:
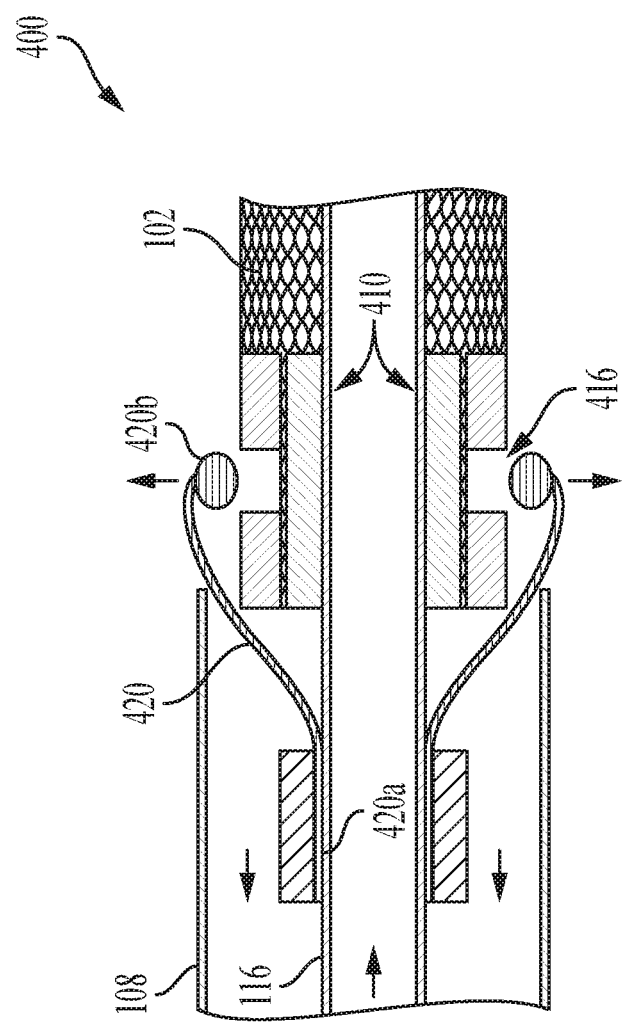
FIG. 4B is a cross-sectional side view of the assembly shown in FIG. 4A after an elongated member of the system has been partially withdrawn, in accordance with embodiments of the present technology.
Figure 4C:
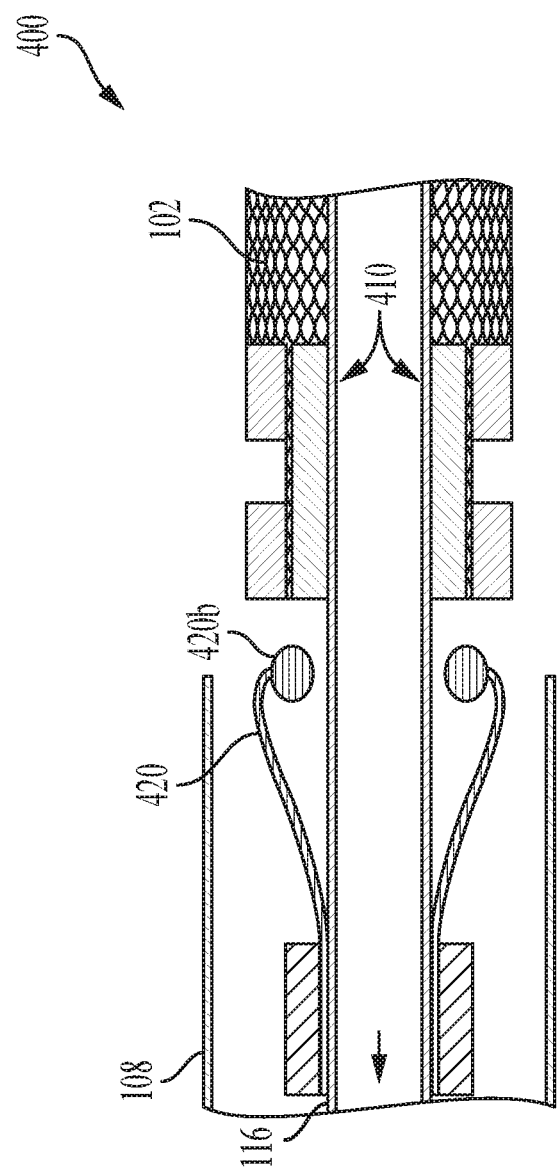
FIG. 4C is a cross-sectional side view of the assembly shown in FIG. 4B after the elongated member has been further withdrawn, in accordance with embodiments of the present technology.

FIGS. 4A-4C are cross-sectional side views of a coupling assembly 400 ("assembly 400"), in accordance with embodiments of the present technology. FIG. 4A shows the assembly 400 while the occlusive member 102 is in a constrained state during delivery, FIG. 4B shows the assembly 400 during deployment of the occlusive member 102, and FIG. 4C shows the assembly 400 after deployment of the occlusive member 102. As shown in FIG. 4A, during delivery of the occlusive member 102 through the vasculature, the occlusive member 102 may be disposed around the conduit 116 and generally contained within or surrounded by the second elongated shaft 108. In some embodiments, the conduit 116 can have a diameter ($D_1$) of at least about 1 French or 0.012 inches, and the second elongated shaft 108 can have a larger diameter ($D_2$) of at least about 2 French or 0.24 inches. A proximal portion 102a of the occlusive member 102 is coupled to a coupler 410, which may correspond to the first coupler 112 previously described with reference to FIGS. 1A-3G. The coupler 410 can be slidably and/or rotatably coupled to the conduit 116 such that the coupler 410 and conduit 116 can move axially (e.g., distally and proximally) and/or rotate relative to one another.

The coupler 410 can secure the occlusive member 102 thereto (e.g., via crimping or other attachment means) and prevent the occlusive member 102 from sliding proximally beyond the coupler 410. As shown in FIG. 4A, the coupler 410 can include an inner band 418 disposed around the conduit 116, and first and second outer bands 412, 414 each disposed around the inner band 418. The proximal portion 102a of the occlusive member 102 is disposed and fixedly secured to the coupler 310 between the inner band 418 and first and second outer bands 412, 414. The first outer band 412 is distal to and spaced apart from the second outer band 414 to define an intermediate region 416 therebetween that corresponds to a void or gap. The void or gap is recessed relative to the radially outermost surfaces of the first and/or second outer bands 412, 414. Other embodiments of the coupler 410 are shown and described with reference to FIGS. 5 and 6.

As shown in FIG. 4A, one or more securing members 420 ("securing member 420") may be removably coupled to the coupler 410, and therein to the occlusive member 102. The securing member 420 can be an elongate structure including a proximal end portion 420a and a distal end portion 420b. In some embodiments, the securing member 420 may be a single structure disposed around the conduit 116, whereas in other embodiments the securing member 420 may include one or more independent structures. For example, the securing member 420 shown in FIG. 4A includes two independent structures. The securing member 420, including the proximal and/or distal end portions 420a, 420b, may be formed at least in part from a superelastic and/or radiopaque material, such as nitinol. The securing member 420 may also be formed at least in part from platinum, chromium cobalt ("CrCo") alloys, stainless steel alloys, or combinations thereof (including nitinol). The securing member 420 can include a continuous and/or contiguous surface that extends along the proximal and distal end portions 420a, 420b. In some embodiments, the securing member 420 may be heat treated to maintain a particular shape (e.g., a curved shape). For example, as shown in FIG. 4A, the portion of the securing member 420 adjacent the distal end portion 420b is curved inwardly toward the conduit 116. As explained in detail elsewhere herein, such a shape can enable the distal end portion 420b to move radially away from the conduit 116 when the conduit 116 is moved in a distal direction relative to the coupler 410 and/or occlusive member 102. In some embodiments, the securing member 420 may have a substantially linear or straight shape.

The proximal end portion 420a of the securing member 420 can be secured to the conduit 116, e.g., via a stop 422 (e.g., a bumper) such that the proximal end portion 420a, stop 422, and/or conduit 116 are fixed in position relative to one another. The securing member 420 and/or stop 422 may correspond to the second coupler 114 previously described with reference to FIGS. 1A-3F. The stop 422 can limit axial movement of the coupler 310 along the conduit 116. Additionally, since the coupler 410 is axially moveable along the conduit 116, the stop 422 can abut and provide a pushing force on the coupler 410 during distal advancement of the occlusive member 102 toward a target delivery site. The stop 422 may be formed at least in part from a radiopaque material, such as platinum, nitinol, CrCo alloys, stainless steel alloys, or combinations thereof.

The distal end portion 420b can have a circular, cuboidal, hexagonal or other shape that is atraumatic, and a cross-sectional dimension that is larger than a cross-sectional dimension of at least a portion of the rest of the securing member 420. The distal end portion 420b can be positioned between or within a portion of the coupler 410. As shown in FIG. 4A, the distal end portion 420b is positioned radially outward of the inner band 418 and occlusive member 102, and axially between the first and second outer bands 412, 414. The radially inwardmost surface of the distal end portion 420b is radially inward of the outermost surface of the first and/or second outer bands 412, 414. As explained in detail elsewhere herein, the distal end portion 420b is removably coupled to the coupler 310, and therein to the occlusive member 102. In some embodiments, the securing member 420 remains coupled to the coupler 410 during delivery (e.g., advancement of the occlusive member 102 toward the target site), and can only be uncoupled from the coupler 410 when the distal end portion 420b is distally beyond a distal terminus of the surrounding second elongated shaft 108. Stated differently, the securing member 420 remains coupled to the coupler 410 while the coupler 410 and/or distal end portion 420b are contained within the second elongated shaft 108. In such embodiments, the distance or spacing in a radial direction between the second elongated shaft 108 and radially outermost surface of the second outer band 414 may be less than a dimension ($D_3$) of the distal end portion 420b, such that the spacing and second outer band 414 prevent complete removal of the distal end portion 420*b* from the intermediate region 416.

FIG. 4B is a cross-sectional side view of the assembly 400 shown in FIG. 4A after the second elongated shaft 108 is at least partially withdrawn relative to the occlusive member 102, in accordance with embodiments of the present technology. As shown in FIG. 4B, the occlusive member 102, the coupler 410, and at least a portion of the securing member 420 are distally beyond a distal terminus of the second elongated shaft 108. In such configurations, the securing member 420 can be decoupled from the coupler 410 and thereby cause the occlusive member 102 to be released from the securing member 420. As the second elongated shaft 108 is withdrawn proximally relative to the occlusive member 102 and/or conduit 116, the securing member 420, or more particularly the distal end portion 420*b*, moves radially away from the coupler 410 and thereby decouples itself from the coupler 410 and occlusive member 102. That is, the securing member 420 may be configured (e.g., heat treated) to self-expand such that after the second elongated shaft 108 is withdrawn, the distal end portion 420*b* self-expands and thereby decouples itself from the coupler 410.

As described in additional detail elsewhere herein (e.g., with reference to FIG. 8E-8H), in some embodiments the distal end portion 420*b* remains positioned within the intermediate region 416 and thus coupled to the coupler 410 even after the second elongated shaft 108 is proximally withdrawn. That is, withdrawing the second elongated shaft 108 proximally beyond the distal end portion 420*b* may not by itself decouple the securing member 420 from the coupler 410 and/or occlusive member 102. This may be in part because the distal end (not shown) of the conduit 116 can exert a distally axial force on the occlusive member 102, which generates tension between the coupler 410 and distal end portion 420*b*. In such embodiments, the securing member 420 may be decoupled from the coupler 410 only after distally moving the conduit 116 relative to the coupler 410. In doing so, the proximal end portion 420*a* is moved toward the coupler 410, thereby urging the distal end portion 420*b* radially outward and decoupling the securing member 420 from the coupler 410 and/or occlusive member 102. Stated differently, distal movement of the conduit 116 relative to the coupler 410 can cause the distal end portion 420*b* of the securing member 420 to move radially away from the conduit 116 and thereby decouple the coupler 410 and occlusive member 102 from the securing member 420.

FIG. 4C is a cross-sectional side view of the assembly 400 shown in 4B after the occlusive member 102 further advanced distally relative to the second elongated shaft 108, in accordance with embodiments of the present technology. As shown in FIG. 4C, after the distal end portion 420*b* is uncoupled from the coupler 410, and therein the occlusive member 102, the distal end portion 420*b* may migrate (e.g., as a result of heat treating) toward the conduit 116 as the conduit 116 is withdrawn proximally. As explained elsewhere herein, after the occlusive member 102 is released from the securing member 420 and/or deployed (e.g., within an aneurysm), the occlusive member 102 may self-expand to an expanded state.

Figure 5:
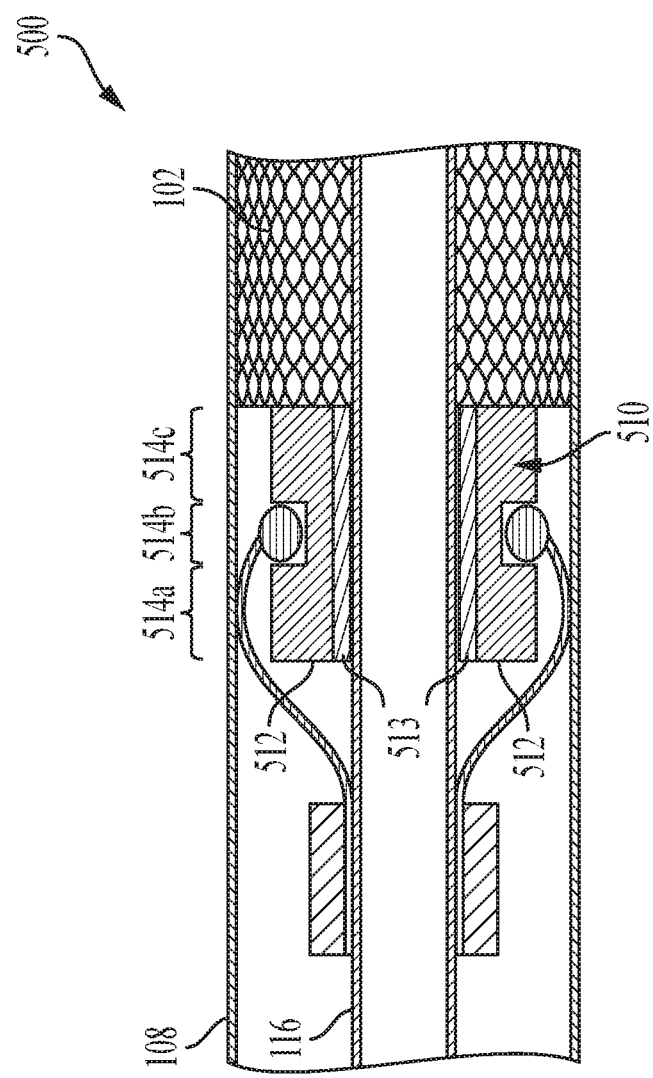
FIGS. 5-7 are cross-sectional side views of other embodiments of the assembly shown in FIG. 4A, in accordance with embodiments of the present technology.

FIG. 5 is a cross-sectional side view of an embodiment of the assembly 400 shown in FIG. 4A, in accordance with embodiments of the present technology. As shown in FIG. 5, the assembly 500 includes many of the features shown and described with reference to FIG. 4A, but includes a second coupler 510 (or "coupler 510") differing from the coupler 410 previously described. The coupler 510 is formed of outer and inners bands 512, 513 disposed around the conduit 116. The outer band 512 may include proximal region 514*a*, a distal region 514*c*, and an intermediate region 514*b* therebetween. The intermediate region 514*b* can be generally similar in function to the intermediate region 416 previously described with reference to FIG. 4A. That is, the intermediate region 514*b* can define a gap between the proximal and distal regions 514*a*, 514*c* that is recessed relative to the radially outermost surfaces of the proximal and/or distal regions 514*a*, 514*c*. The inner band 513 may be surrounded by the outer band 512. The occlusive member 102 can be coupled to the coupler 510, e.g., via a proximal portion of the occlusive member 102 disposed between the outer band 512 and the inner band 513. The coupler 510 can be slidably and/or rotatably coupled to the conduit 116 such that the coupler 510 and conduit 116 can move axially (e.g., distally and proximally) and/or rotate relative to one another.

Figure 6:
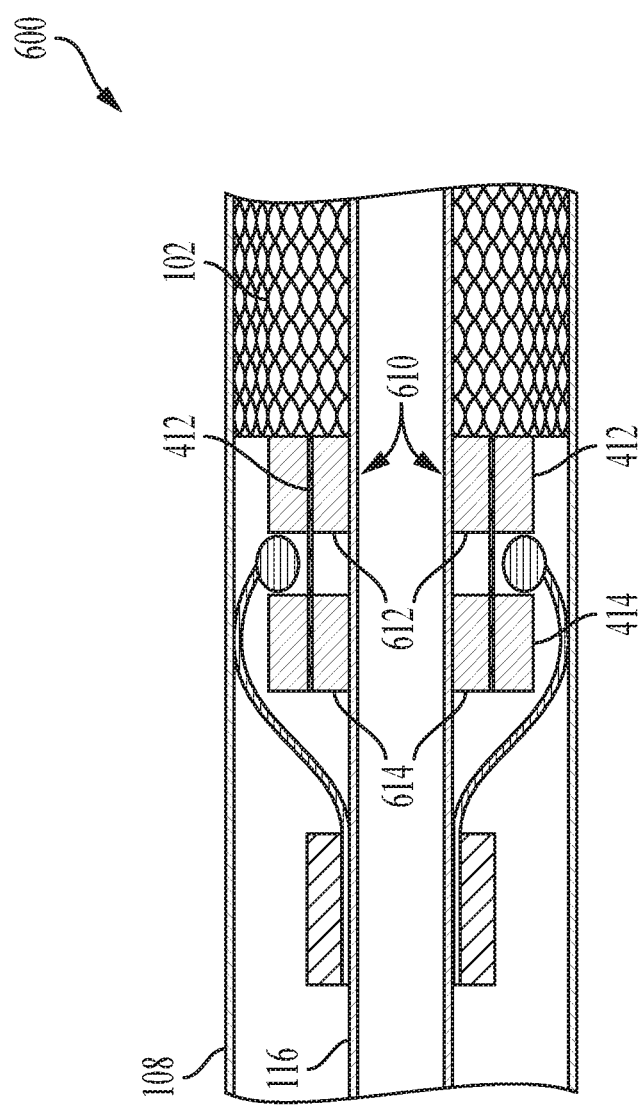

FIG. 6 is a cross-sectional side view of another embodiment of the assembly 400 shown in FIG. 4A, in accordance with embodiments of the present technology. As shown in FIG. 6, the assembly 600 has many of the features shown and described with reference to FIG. 4A, but includes a coupler 612 differing from the coupler 410 previously described. The coupler 610 includes first and second outer bands 412, 414, as described with reference to FIG. 4A, as well as first and second inner bands 612, 614. The first and second outer bands 412, 414 are disposed around the first and second inner bands 612, 614, respectively, which are disposed around the conduit 116. The coupler 610 can be slidably and/or rotatably coupled to the conduit 116 such that the coupler 610 and conduit 116 can move axially (e.g., distally and proximally) and/or rotate relative to one another.

Figure 7:
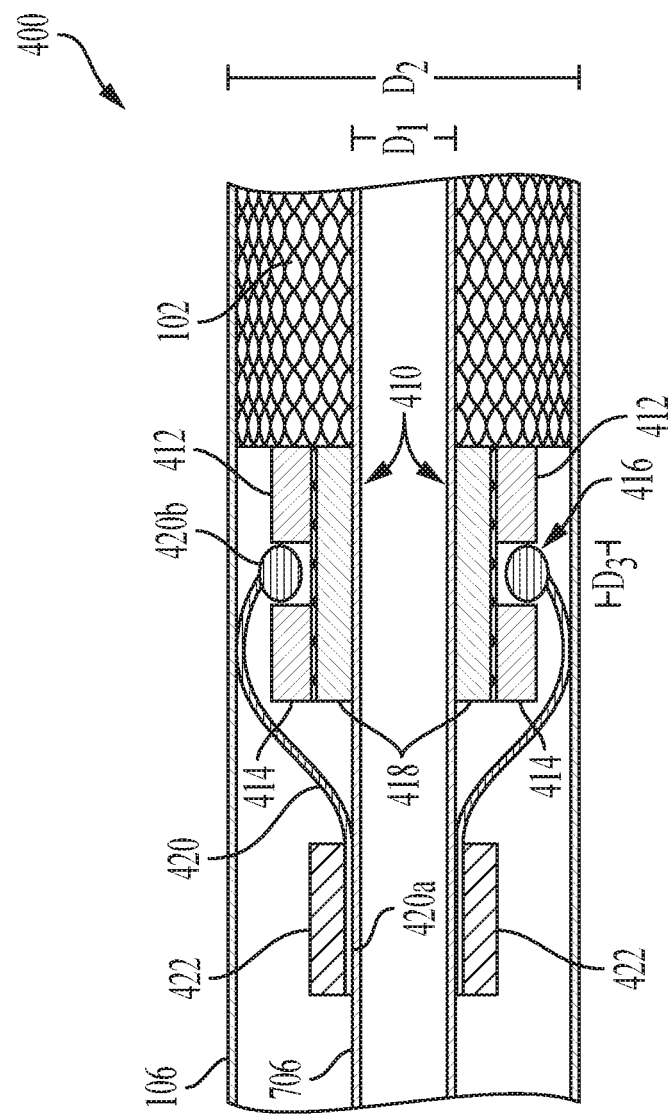

In some embodiments, for example as shown in FIG. 7, the conduit may be formed of a microcatheter. Using a microcatheter device for embodiments that inject an embolic element therethrough may be particularly advantageous because microcatheters are generally built as leak proof devices.

As shown in FIG. 7, the occlusive member 102 is disposed around the second elongated shaft 108 and generally contained within or surrounded by the elongated shaft 108. The second elongated shaft 108 can have a diameter ($D_1$) of at least about 1 French or 0.012 inches, and the elongated shaft 108 can have a larger diameter ($D_2$) of at least about 2 French or 0.24 inches. The occlusive member 102 is coupled to the coupler 410, which can slidably and/or rotatably coupled to the second elongated shaft 108 such that the coupler 410 and second elongated shaft 108 can move axially (e.g., distally and proximally) and/or rotate relative to one another.

FIGS. 8A-8G illustrate a method for delivering an occlusive member to a target site after resheathing the occlusive member within an elongated shaft and/or repositioning the elongated shaft within the target site, in accordance with embodiments of the present technology. As previously described, embodiments of the present technology are directed to advancing an occlusive member via a delivery system to a target site, such as an aneurysm cavity, and deploying the occlusive member thereto. In practice, advancing the occlusive member may require the delivery system to be arranged in a particular position, such as in a center portion of the aneurysm cavity and not too close to a sidewall of the aneurysm. In such instances where the delivery system is improperly advanced to the target site, the delivery system may need to be withdrawn therefrom and repositioned to allow the occlusive member to be properly deployed. In some embodiments, the occlusive member may be partially deployed and thus need to be resheathed (e.g., within a delivery catheter) prior to repositioning. As used herein, "resheathing" can refer to a method or mechanism that withdraws a partially deployed occlusive member back into an elongated member or shaft of the delivery system.

Figure 8B:
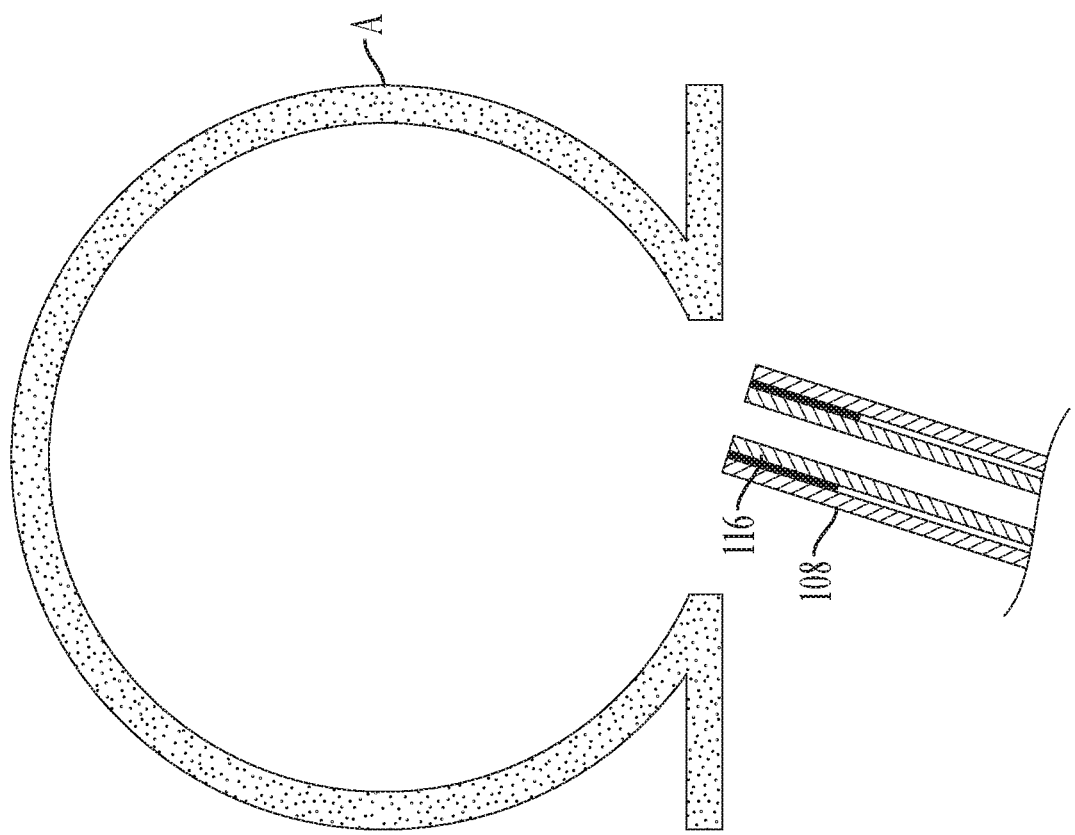
Figure 8A:
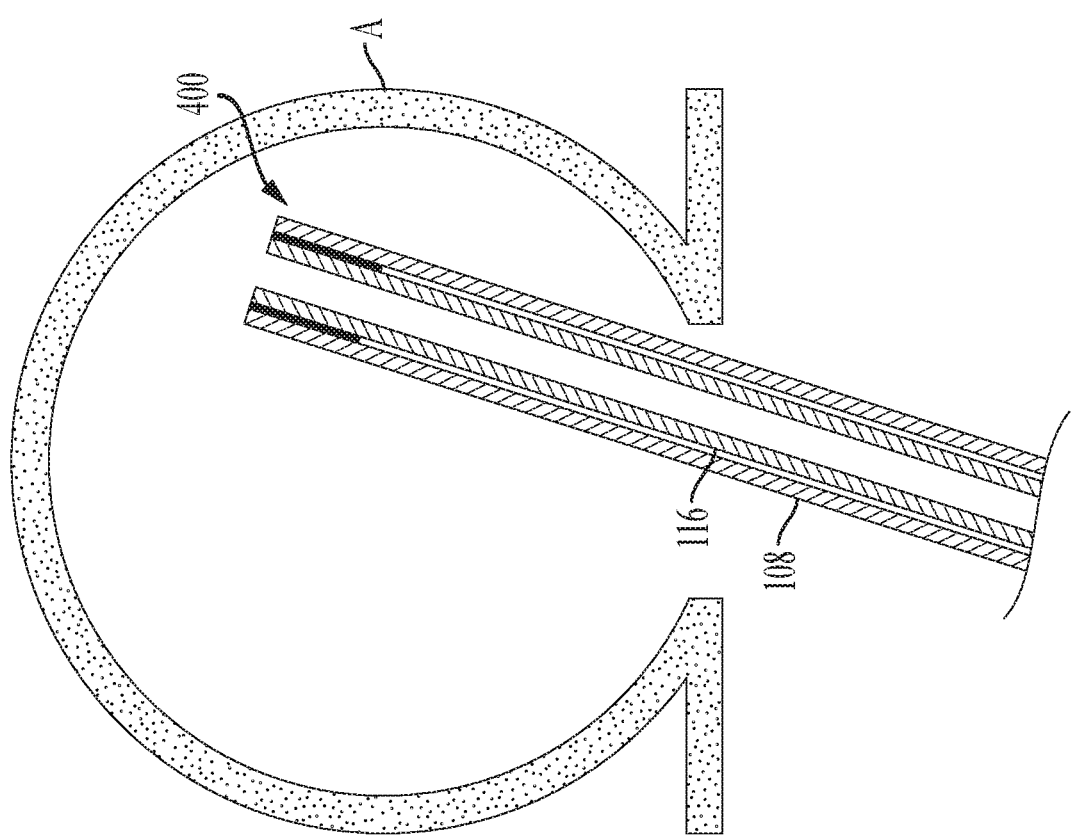

FIG. 8A illustrates a delivery system for deploying an occlusive member to a target site, such as a cerebral aneurysm (A). The delivery system includes the conduit 116 (e.g., a hypotube), second elongated shaft 108 (e.g., a microcatheter) surrounding a portion of the conduit 116, first elongated shaft 108 (e.g., a delivery catheter) surrounding a portion of the second elongated shaft 108, and assembly 400 disposed within a lumen between the conduit 116 and second elongated shaft 108. As shown in FIG. 8A, the delivery system is improperly positioned within the aneurysm (A) and needs to be withdrawn and repositioned before fully deploying the occlusive member. In some embodiments, if the occlusive member of the detachment assembly 400 has been partially deployed (i.e., not fully deployed), the occlusive member can be resheathed within the second elongated shaft 108 via the assembly 400 prior to withdrawing the conduit 116 and second elongated shaft 108. FIG. 8B illustrates the delivery system after the conduit 116 and second elongated shaft 108 have been withdrawn from the aneurysm (A) prior to repositioning.

FIG. 8C illustrates the delivery system after being properly positioned within the aneurysm (A). As shown in FIG. 8D, which generally illustrates the assembly 400, the occlusive member 102 is coupled to the coupler 410, which is removably coupled to the conduit 116 via the securing member 420, as previously described. The configuration of the assembly 400 prevents or inhibits the coupler 410 and occlusive member 102 from being decoupled from the securing member 420 and conduit 116 while at least a portion of the securing member 420 is contained within the second elongated shaft 108.

Figures 8E, 8F:
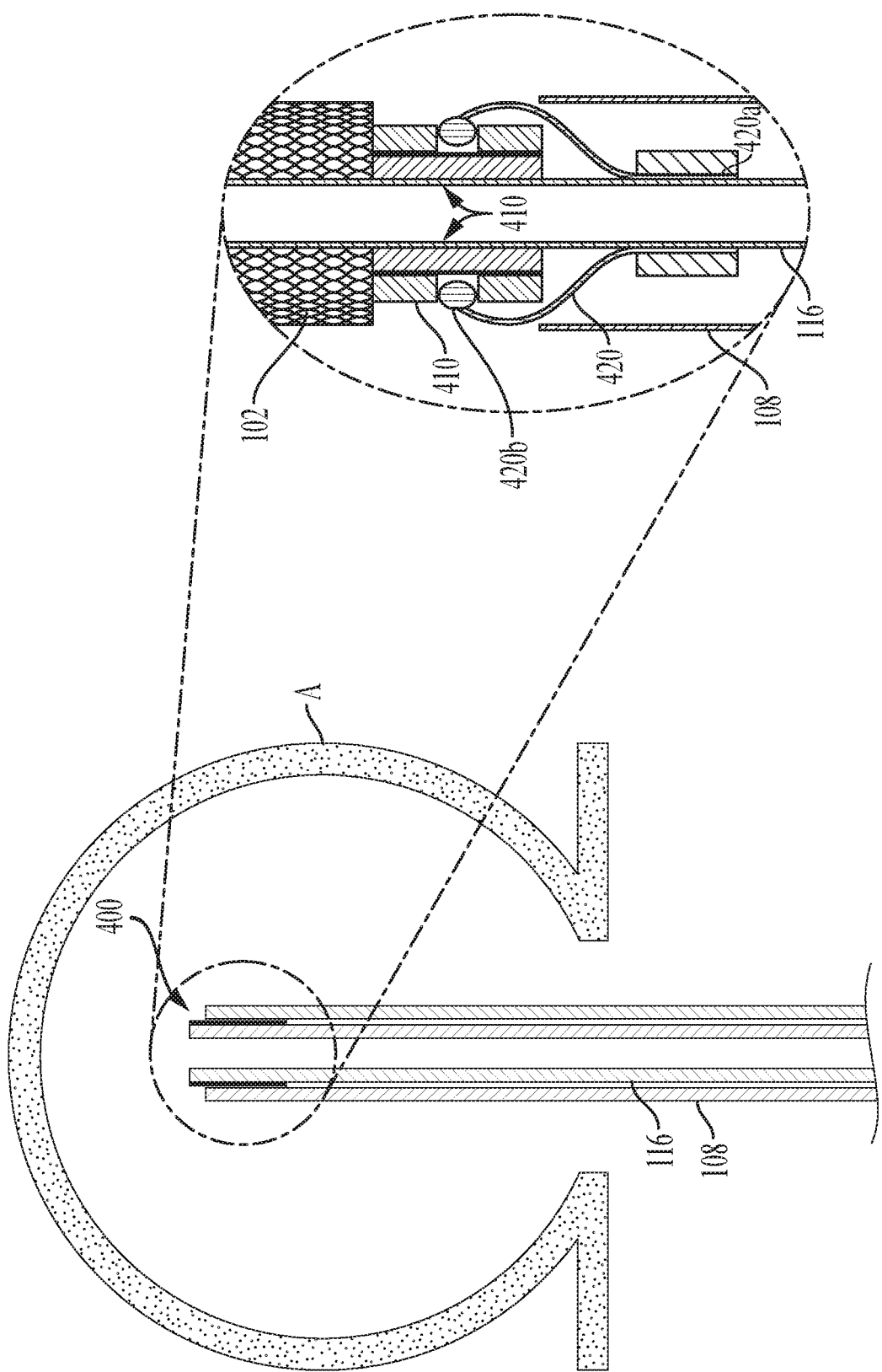

FIG. 8E illustrates the delivery system after the second elongated shaft 108 is partially proximally withdrawn relative to the conduit 116. For illustrative purposes, the occlusive member 102 and the expansion thereof are not illustrated in FIGS. 8E and 8F. As shown in FIG. 8F, the second elongated shaft 108 is withdrawn proximally beyond the distal end portion 420b of the securing member 420. As described elsewhere herein (e.g., with reference to FIGS. 4A and 4B), just withdrawing the second elongated shaft 108 by itself may cause the securing member 420 to uncouple from the coupler 410. In some embodiments though, as also described elsewhere herein, just withdrawing the second elongated shaft 108 by itself may not uncouple the securing member 420 from the coupler 410. In such embodiments, distal movement of the conduit 116, and therein the proximal end portion 420a of the securing member 420, relative to the coupler 410 after the second elongated shaft 108 is withdrawn proximally beyond the distal end portion 420b may be required to decouple the coupler 410 and occlusive member 102 from the securing member 420. As previously described, distal movement of the conduit 116 relative to the coupler 410 may be required to decouple the coupler because the conduit 116 exerts a distally axial force on the occlusive member 102 which generates a tension between the coupler 410 and distal end portion 420b. The tension may maintain the coupled arrangement between the coupler 410 and securing member 420 after the second elongated shaft 108 is withdrawn proximally beyond the distal end portion 420b.

FIGS. 8G and 8H illustrate the delivery system after the conduit 116 is advanced distally relative to the coupler 410 and occlusive member 102. For illustrative purposes, the occlusive member 102 and the expansion thereof are not illustrated in FIGS. 8G and 8H. As shown in FIG. 8H, advancing the conduit 116 distally relative to the coupler 410 can cause the distal end portion 420b to move radially outward away from the coupler 410, thereby decoupling the occlusive member 102 from the securing member 420. In doing so, the occlusive member 102 may be deployed, e.g., by self-expanding to its expanded state and filling at least a majority of the aneurysm cavity.

CONCLUSION

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A treatment system, comprising:
an occlusive implant configured to be positioned within an aneurysm;
a coupler at a proximal portion of the occlusive implant;
a conduit having a lumen extending therethrough and a distal portion slidably coupled to the coupler such that the conduit is axially movable relative to the coupler, wherein the coupler circumferentially surrounds the conduit; and
a securing member attached to the conduit, the securing member configured to be engaged with the coupler when the securing member is in a radially constrained state, and to be disengaged with the coupler when the securing member is in a radially unconstrained state.

2. The treatment system of claim 1, wherein the occlusive implant comprises an expandable mesh having a constrained state for delivery to the aneurysm and an expanded state in which at least a portion of the mesh is configured to be disposed across a neck of the aneurysm.

3. The treatment system of claim 1, wherein the conduit is configured to convey an embolic element therethrough for delivery to the aneurysm.

4. The treatment system of claim 1, wherein the coupler comprises a recess and wherein the securing member comprises a structure configured to be received within the recess while the securing member is in the radially constrained state.

5. The treatment system of claim 1, wherein distal movement of the conduit relative to the coupler urges the securing member radially away from the coupler.

6. The treatment system of claim 1, further comprising an elongate tubular member having a lumen configured to receive the occlusive implant and conduit therein, wherein the elongate tubular member restrains the securing member in the radially constrained state when overlying the securing member.

7. The treatment system of claim 6, wherein proximal retraction of the elongate tubular member to a position proximal of the securing member causes the securing member to assume the radially unconstrained state.

8. The treatment system of claim 1, wherein, when the securing member is disengaged with the coupler, the conduit can be proximally retracted with respect to the coupler while the occlusive implant remains within the aneurysm.

9. A treatment system, comprising:
a conduit having a distal portion and a lumen extending therethrough;
a coupler slidably coupled to the distal portion such that the coupler is axially movable relative to the conduit, wherein the coupler circumferentially surrounds the conduit;
an occlusive member coupled to the coupler; and
a securing member attached to the conduit proximal to the coupler, the securing member including a distal end portion removably coupled to the coupler.

10. The treatment system of claim 9, wherein the distal portion is moveable between a radially constrained state in which it is coupled with the coupler, and a radially unconstrained state in which it is uncoupled from the coupler.

11. The treatment system of claim 9, wherein the distal portion of the conduit is biased in a direction away from the coupler.

12. The treatment system of claim 9, wherein the occlusive member comprises an expandable mesh having a constrained state for delivery to an aneurysm and an expanded state in which at least a portion of the mesh is configured to be disposed across a neck of the aneurysm.

13. The treatment system of claim 9, wherein the coupler comprises a recess and wherein the securing member comprises a structure configured to be received within the recess while the securing member is in a radially constrained state.

14. The treatment system of claim 9, further comprising a catheter having a lumen configured to receive the occlusive member and conduit therein, wherein the catheter restrains the securing member in a radially constrained state when overlying the securing member.

15. The treatment system of claim 9, wherein, when the securing member is uncoupled from the coupler, the conduit can be proximally retracted with respect to the coupler without moving the occlusive member.

16. A treatment system, comprising:
an occlusive member having a coupler attached thereto, the coupler having a recess along a radially outer surface; and
a conduit slidably movable with respect to the coupler and having a securing member attached thereto, the securing member comprising one or more structures configured to be releasably received within the recess of the coupler, wherein the coupler circumferentially surrounds the conduit.

17. The treatment system of claim 16, wherein the securing member is configured such that the one or more structures are biased away from the recess.

18. The treatment system of claim 16, wherein the securing member is moveable between a radially reduced state in which the one or more structures are received within the recess of the coupler and a radially expanded state in which the one or more structures are not received within the recess of the coupler.

19. The treatment system of claim 16, wherein, while the occlusive member is disposed at a treatment site, when the one or more structures of the securing element are not received within the recess of the coupler, the conduit can be proximally retracted with respect to the coupler without removing the occlusive member from the treatment site.

* * * * *